United States Patent [19]
Gram et al.

[11] Patent Number: 5,858,728
[45] Date of Patent: Jan. 12, 1999

[54] MONOCLONAL ANTIBODY AGAINST LPS CORE

[75] Inventors: Hermann Gram, Weil-Haltingen, Germany; Franco Di Padova, Birsfelden, Switzerland; George Robin Barclay; Ian Raymond Poxton, both of Midlothian, United Kingdom

[73] Assignee: Common Services Agency

[21] Appl. No.: 647,144

[22] Filed: May 9, 1996

Related U.S. Application Data

[63] Continuation of Ser. No. 119,046, Sep. 30, 1993, abandoned.

[30] Foreign Application Priority Data

Mar. 13, 1991 [GB] United Kingdom ............... 9105292

[51] Int. Cl.$^6$ ............................ C12P 21/04; C12P 21/08; C12N 5/06; C07K 16/00
[52] U.S. Cl. ................................... 435/70.21; 435/172.2; 435/340; 435/328; 530/388.4; 530/387.1; 530/387.3
[58] Field of Search ............................ 530/388.4, 387.1, 530/387.3; 435/340, 172.2, 70.21, 328

[56] References Cited

U.S. PATENT DOCUMENTS 5,378,812  1/1995  Siadak .................................. 530/388.4

FOREIGN PATENT DOCUMENTS 8404458  11/1984  WIPO .

OTHER PUBLICATIONS

Riechmann, L. et al, Nature, 332:323–327, Mar. 1988.
Appelmelk, B.J. et al., J. Med. Microbiol., 26:107–114, 1988.
Dunn, D.L. et al., Surg. Forum, 34:142–4, 1983.
Young, L.S. et al., J. Clin Investig, 56: 850–861, 1975.
Nys, M. et al., JID, 162:1087–1095, 1990.
Morrison, S.L. et al., PNAS, 81:6851–6855, Nov. 1984.
Queen, C. et al., PNAS, 86:10029–10033, Dec. 1989.
Winter, G et al., TIPS, 14; 139–143.
LoBuglio, A.F. et al., Immunology, 86:4220–4224, Jun. 1989.
DiPadova, F.E. et al., Bacterial Endotoxin: Recognition and Effector Mechanisms, ed. J. Levin, pp. 325–335, 1993.
Barclay, G.R., Reviews in Medical Microbiology, 1:133–142, 1990.
Fitzer–Schiller, G., The Washington Post, D3, Jan. 19, 1993.
Spaulding, B.J., Bio/Technology, 11:428–429, Apr. 11, 1993.
Stone, R., Science, 259:1243, 26 Feb. 1993.

*Primary Examiner*—Susan A. Loring
*Attorney, Agent, or Firm*—Bell Seltzer Intellectual Property Law Group of Alston & Bird LLP

[57] ABSTRACT

The invention provides monoclonal antibodies (Mabs) which are cross-protective against endotoxemia caused by at least two different Gram-negative bacterial strains having different core structures; and methods of production of these antibodies. By use of the Köhler/Milstein procedure involving immunization of mice with a number of different rough strains of heat-killed Gram-negative bacteria, followed by fusion and proper screening of the resulting hybridomas, such murine MAbs are obtained. The murine MAbs may be chimerized or humanized by known methods. For example, a chimeric MAb of IgG isotype is provided in which the hypervariable regions of the heavy chain have the amino acid sequences: Asp Tyr Tyr Met Thr; Leu Ile Arg Asn Lys Arg Asn Gly Asp Thr Ala Glu Tyr Ser Ala Ser Val Lys; and Gln Gly Arg Gly Tyr Thr Leu Asp Tyr; the hypervariable regions of the light chain have the amino acid sequences: Arg Ala Ser Gln Asn Ile Asn Ile Trp Leu Ser; Lys Ala Ser Asn Leu His Thr; and Leu Gln Gly Gln Ser Tyr Pro Arg Thr; the framework regions in the variable domains are murine and the constant domains are human.

26 Claims, 10 Drawing Sheets

MONOCLONAL ANTIBODY AGAINST LPS CORE

This is a continuation of copending application Ser. No. 08/119,046 filed on 30 Sep., 1993 (the contents of which are incorporated herein by reference), which is national phase application of GB9105292.8 filed 13 Mar., 1991.

The present application, Ser. No. 08/647,144, filed May 9, 1996 is a File Wrapper Continuation of application Ser. No. 08/119,046, filed Sep. 30, 1993, now abandoned.

This invention relates to the prevention, diagnosis and treatment of infectious diseases caused by Gram-negative bacteria and more particularly provides monoclonal antibodies (MAbs) against the lipopolysaccharide (LPS; also called endotoxin) constituent of the gram-negative bacterial membranes.

Enterobacteria are a widely prevalent group of Gram-negative microorganisms which cause serious and frequently lethal infections in patients undergoing certain types of surgery, anti-cancer chemotherapy or immunosupressive treatment or in patients suffering from various trauma, burns or wounds. The severity of the disease ranges from a preliminary, transient and limited episode of bacteremia to a subsequent, fulminant and life-threatening conditon of endotoxemia (also called septic shock) characterized, in particular, by a severe hypotension.

Some 425,000 cases of severe Gram-negative bacteremia occur yearly in the USA with an overall mortality of about 25%. The majority of these infections are due to the most common pathogen *Escherichia coli*, followed in frequency by *Klebsiella pneumoniae. Pseudomonas aeruginosa*. Proteus. Enterobacter and Serratia. All Gram-negative bacteria are characterized by a specific type of outer membrane which comprises a lipopolysaccharide (LPS) as major constituent. LPS plays an essential immunologic and physiopathologic role in the infections and is the major causative agent of septic shock.

Although the LPS constituent varies from one species to another, it may be generally described with reference to FIG. 1 as consisting of three structural regions: Lipid A whose lipid portion is embedded in the outer leaflet of the outer membrane; the oligosaccharide core region and the O-specific outer region. Lipid A has the same basic structure in practically all enterobacteria and is the main endotoxic determinant. The core region shows a high degree of similarity among bacterial genera. It usually consists of a limited number of sugars. The inner core region is constituted of heptose and 2-Keto-3-deoxy-octonate (KDO) residues while the outer core region comprises galactose, glucose or N-acetyl-D-glucosamine residues displayed in various manners, depending upon the strain. For example, outer core structures R1 to R4 of different *E. coli* strains are shown in FIG. 2. The O-specific outer region (also called O-specific side chain) is highly variable and is composed of repeated oligosaccharide units characteristic of the species. LPS molecules on the surface of a single cell do not have a constant amount of oligosaccharide units.

The presence of the O-specific side chain confers to a culture of a wild type bacterium a smooth aspect. This is the reason why wild type bacteria are usually referred to as smooth bacteria in contrast with rough mutants which lack the O-specific side chain and, sometimes, part of the core region and the cultures of which show a rough aspect. The different types of rough mutants from Salmonella are conventionally designated by the terms Ra, Rb, Rc, Rd and Re. As seen from FIG. 1, the LPS of all of them comprises the lipid A structure while the Ra mutant is characterised by a complete core region, the Rb mutant is characterised by the absence of N-acetyl-D-glucosamine residue, the Rc mutant is characterised by the absence of N-acetyl-D-glucosamine and galactose residues, the Rd mutant is characterised by the absence of any residue constituting the outer core and the Re mutant is characterised by the sole KDO region attached to lipid A.

Since treatments for the toxic effect of LPS are not available. attention has been focused on immunologic methods as an alternative or additional treatment to antibiotic therapy to prevent or control such infections. Current immunotherapy involves the administration of conventional polyclonal antisera and hyperimmune sera to bolster the native defenses of patients against the adverse effects of bacteria, for example, by enhancing opsonization and phagocytosis of the bacterial cells or by neutralization of the biological activity of LPS. However, the effectiveness of the antisera greatly varies depending upon a large number of factors including, for example, the composition and titre of the specific antibodies, which cannot be easily standardized.

To overcome the limited efficacy of serotherapy, it has been proposed to use cross-reactive MAbs. Cross-reactivity is of two kinds, which may be described as horizontal and vertical. By vertical cross-reactivity is meant that the MAb reacts with essentially all smooth LPS molecules of a particular bacterial strain, independent of the length of the O-specific side-chain. By horizontal cross-reactivity is meant that the MAb reacts with LPS having different core structures. This is necessary because therapy must be started as soon as the bacteremia has been empirically diagnosed, rather than waiting for the identification of the pathogen, which may take several days.

Such MAbs must recognize antigenic determinants located in the LPS structure which is shared by most enterobacteria i.e. Lipid A and the core region. They may be obtained by the well-known Kohler & Milstein method which, in particular comprises conventionally immunizing mice with an immunogen in which the inner antigenic epitopes of LPS are immediately available for raising antibodies. Suitable immunogens include heat-killed rough mutants of an enterobacterium e.g. the J5 strain of *E. coli*. Purified LPS is less suitable as an immunogen.

A MAb expected to be useful for preventing or treating bacteremia should not only be cross-reactive but also cross-protective against the infections caused by the most common toxic bacteria. However, it has been reported in several scientific articles, for example, in Pollack et al. J. Infect. Dis. (1989) 159 (2): 168, that the large majority of antibodies raised against the conventional immunogens cited above cross-react poorly and, unfortunately fail to be protective against infections. MAbs have often been described as reactive on the basis of binding experiments involving rough rather than smooth LPS, and the lack of protectivity of these MAbs may be due to the fact that, in wild-type smooth LPS, the epitope for which the antibody is specific is not available, being hindered by the core region or the O-specific side chain. In particular, MAbs recognizing epitopes in the Lipid A part of the LPS molecule are generally ineffective.

It has now been found that monoclonal antibodies recognizing epitopes in the core region of the LPS molecule and having both vertical and horizontal cross-reactivity and also cross-protectivity can be obtained by modified and improved immunization and screening procedures. Such MAbs are initially obtained in murine form and may be converted by known recombinant DNA techniques into chimeric (murine variable region, human constant region) or humanized (murine hypervariable regions, human framework and constant region) forms.

Accordingly the present invention provides a monoclonal antibody which recognizes an epitope in the core region of the LPS molecule and which is cross-protective against endotoxemia caused by at least two different Gram-negative bacterial strains having different core structures.

Preferably the MAb recognises an epitope which is already present in the Rc core structure of E. coli and is also present in the complete core.

In E. coli, the MAb of the invention preferably reacts with all common smooth strain isolates, and preferably also with rough strain mutants of all five core types (R1, R2, R3, R4, and K12). Preferably the MAb is also reactive with different strains of Salmonella.

In contrast to the immunization protocols described in the prior art, in which generally a single type of LPS (normally as heat-killed bacteria bearing the specific type of LPS) is used as immunogen, MAbs of the present invention may be produced by an immunization protocoll in which the animal to be immunized is exposed to a plurality of types of LPS molecule. This may be done either by immunization with a cocktail of different LPS types physically mixed together, or by immunizing in sequence by individual different LPS types. In both cases it is prefered to use heat-killed bacteria rather than purified LPS molecules. Other possible immunogens include bacteria killed by means other than heat (e.g. by formaldehyde) and LPS molecules linked to protein carriers.

The animal to be immunized is preferably a mouse, which may be of the Balb-c strain. It may however be preferable to use mice of different genetic background, for example New Zealand Black or Swiss Webster mice, which are capable of giving a wider immune response. The immunogen may be administered intravenously, or, preferably, subcutaneously, for example in the foot pad.

In a first preferred method, mice are immunized with a single cocktail of different strains of heat-killed bacteria, preferably rough strains having a complete core, for example a mixture of R1, R2, R3 and R4 strains of Ra E. coli. Alternatively two or more such cocktails, which may be different, may be given on different occasions. For example, injection of a mixture of E. coli R2 and R3 and Salmonella minnesota R60 may be followed a week later by a mixture of E. coli R1, R4 and 018 rough strain, and then the two injections repeated at further weekly intervals.

In a second preferred method, mice are immunized sequentially with a number of different rough strains of heat-killed bacteria, only one strain being administered at any one time. For example mice may be immunized with Pseudomonas PAC 605 rough mutant followed by E. coli R1, R2 and R3 at monthly intervals.

Before any cell fusion is carried out between mouse myeloma cells and spleen cells from the immunized animal, there is preferably an initial screening step in which the strength and plurality of the immune response of the immunized animal is evaluated by testing the serum of the animal. Animals showing a strong immune response are subjected to a booster immunization and the spleen cells of these strongly-responding and re-immunized mice are used for cell fusion to make hybridomas by the conventional Köhler-Milstein technique. The booster immunization is preferably by a cocktail of different rough strain E. coli, even if the primary immunization was carried out by the second preferred method (sequential administration).

The resulting hybridomas are then screened for the cross-reactivity of the antibodies they produce, using the standard ELISA and Western blotting methods described below. In contrast to prior art methods, an initial screening is preferably carried out using a series of mixtures of different smooth and rough LPS types to select those MAbs reacting with a wide range of LPS molecules. In this way, widely cross-reactive MAbs can already be identified at the initial screening stage. For example, each hybridoma supernatant may be screened by testing for reactivity in the ELISA assay with seven different LPS cocktails and a control, according to the following scheme:

1) Smooth strains: EcO4–O6+O16+O18K
2) Smooth strains: EcO12–O15+O86
3) Rough complete core: EcR1+R4
4) Rough complete core: EcR2+EcR3+EcK12+Sm R60
5) Rc core: Ec J5+St878
6) Rc/Rd/Re core: Sm R5–Sm R7+Sm R4+Ec F515+Sm R595
7) Lipid A: derived from Ec K12 & Sm R595
8) Negative control: BSA (Ec=E. coli, Sm=Salmonella minnesota, St=S. typhimurium, BSA=bovine serum albumin)

MAbs found to have good cross-reactivity are then screened further to select those which are not only cross-reactive, but also cross-protective. This may be done using the following in vitro bioassay:

Inhibition of LPS-induced IL-6 secretion by murine peritoneal macrophages

Several monokines including Tumor Necrosis Factor (TNF), IL-1 and IL-6 (also called Interferon-β2) mediate many of the pathophysio-logical events associated with gram-negative sepsis and its accompanying endotoxemia. These monokines are secreted by macrophages, both in vitro and in vivo, in response to LPS. A protective anti-LPS antibody blocks the macrophage stimulation as shown in the following assay:

Murine peritoneal cells are obtained by peritoneal lavage with 0.34M sucrose in distilled water. Peritoneal cells are seeded at $5.10^5$ cells/ml in 0.2 ml serum free medium (IMDM-ATL, Schreier and Tees, Immunological Methods, Vol. II, Acad. Press (1981):263) and cultured for 4 hrs at 37° C. (i) in the presence or absence of LPS e.g. LPS from E. coli R1 (0.05 ng/ml); E. coli R2 (0.05 ng/ml); E. coli R3 (0.05 ng/ml) and E. coli R4 (0.05 ng/ml); and (ii) in the presence or absence of a purified, endotoxin-free antibody the final concentration of which ranges from 0.05 ng to 50 $\mu$g/ml. The supernatants are recovered and the amount of IL-6 present in the supernatants is then measured using the IL-6 dependent hybridoma cell-line B13.29 (Aarden et al., Eur. J. Immunol. 1987. 17, 1911) as follows:

B13.29 cells are seeded at $2.5\times10^4$ cells/ml in serum free medium and cultured for 72 hrs in the absence of IL-6 and in the presence or absence of culture supernatant. Aliquots of the cultures (200 $\mu$l/well) are distributed in flat bottomed microtitre plates. IL-6 concentration in the supernatants is calculated in relation to a standard curve of IL-6.

For the purposes of this patent specification, a MAb is regarded as being protective against a given LPS if it gives in the above assay a reduction of IL-6 secretion of at least 50% when tested at a concentration of 5 $\mu$g/ml, the concentration of purified LPS being 0.05 ng/ml for rough LPS and correspondingly higher for the less active smooth types. A MAb is cross-protective if it is protective against at least two LPS having different core structures. Preferred cross-protective MAbs are cross-protective against LPS from different bacterial genera.

Prefered MAbs of the invention are of the IgG isotype.

By the use of the above immunization and screening methods, a number of novel mouse anti-LPS antibodies have been found which cross-react with several LPS of different genera and exhibit substantial cross-protective activity and that it is possible to construct other LPS binding molecules derived from these monoclonal antibodies and having the same characteristics since they share regions which determine the binding specificity i.e. the hypervariable regions. In particular, four preferred murine monoclonals according to the invention are hereinafter designated WN1 222-5 (isotype IgG2a). WN1 58-9 (IgG2b), H1 61-2 (IgG1), and SZ27 19.16.07 (IgG2a). Of these, the first two are particularly preferred.

Natural immunoglobulins or antibodies comprise a generally Y-shaped molecule built up of two identical heavy chains and two identical eight chains, and having an antigen-binding site at the end of each upper arm. The remainder of the structure, in particular the stem of the Y, mediates effector functions associated with the immunoglobulins. The general structure of an antibody of the IgG class is shown schematically in FIG. 3A. Both heavy and light chains comprise a variable domain and a constant part. An antigen binding site consists of the variable domain of a heavy chain ($V_H$) associated with the variable domain of a light chain ($V_L$). The variable domains of the heavy and light chains have the same general structure which is illustrated in FIG. 3B.

More particularly, the antigen binding characteristics of an antibody are essentially determined by 3 specific regions in the variable domain of the heavy and light chains which are called hypervariable regions or complementary determining regions (CDRs). As shown in FIG. 3B, these 3 hypervariable regions alternate with 4 framework regions, (FRs) whose sequences are relatively conserved and which are not directly involved in binding. The CDRs form loops and are held in close proximity by the framework regions which largely adopt a β-sheet conformation. The CDRs of a heavy chain together with the CDRs of the associated light chain essentially constitute each of the two antigen binding sites of the antibody molecule.

The determination as to what constitutes a FR or a CDR region is usually, made by comparing the amino acid sequence of a number of antibodies raised in the same species. The general rules for identifying the CDR and FR regions are given in Table I.

Furthermore, it has been recently found that the contribution made by a light chain variable domain to the energetics of binding is small compared to that made by the associated heavy chain variable domain and that isolated heavy chain variable domains have an antigen binding activity of their own. Such molecules, now commonly referred to as single domain antibodies, may be regarded as having an antigen binding site, even in the absence of an associated $V_L$ domain.

In view of the foregoing, the invention provides a LPS binding molecule which comprises at least one antigen binding site comprising at least one domain which comprises in sequence, the hypervariable regions hCDR1, hCDR2 and hCDR3; (domains h222-5 and h58-9)
said hCDR1 having the amino acid sequence Asp Tyr Tyr Met Thr which are amino acids 31–35 of SEQ ID NO:2 or SEQ ID NO:4;
said hCDR2 having the amino acid sequence 50–67 of SEQ ID NO:2;
  wherein amino acid 54 is Lys or Tyr and amino acid 67 is Lys or Arg;
said hCDR3 having the amino acid sequence Gln Gly Arg Gly Tyr Thr Leu Asp Tyr (amino acids 101–109 of SEQ ID NO:2 or SEQ ID NO:4);
and direct equivalents thereof.

Preferred is the hypervariable region hCDR2 in which amino acid 54 is Lys and amino acid 67 (amino acids 56–67 is Lys (h222-5, amino acids 50–67of SEQ ID NO:2) or in which amino acid 54 is Tyr and amino acid 67, amino acids 50–67 of SEQ ID NO:4 is Arg (h58-9). More preferred is the hypervariable region hCDR2 in which amino acid 54 is Lys and amino acid 67 is Lys (as in amino acids 50–67 of SEQ ID NO:2).

In a first aspect of the invention, the LPS binding molecule comprises an antigen binding site comprising a single domain.

In a second aspect of the invention, the LPS binding molecule comprises at least one antigen binding site comprising:
a) a first domain comprising in sequence the hypervariable regions hCDR1, hCDR2 and hCDR3, as defined above and,
b) a second domain comprising in sequence the hypervariable regions lCDR1, lCDR2 and lCDR3; (domains 1222-5 and 158-9 [1222-5 or 158-9 stands for light 222-5 or light 58-9])
  said lCDR1 having the amino acid sequence of amino acids 24–34 of SEQ ID NO:6
wherein amino acid 26 is Ser or Arg and amino acid 27 is Gln or Leu;
  said lCDR2 having the amino acid sequence Lys Ala Ser Asn Leu His Thr which are amino acids 50–56 of SEQ ID NO:6 or SEQ ID NO:8);
  said lCDR3 having the amino acid sequence Leu Gln Gly Gln Ser Tyr Pro Arg Thr which are amino acids 89–97 of SEQ ID NO:6 or SEQ ID NO:8;
  and direct equivalents thereof.

Preferred is the hypervariable region lCDR1 in which amino acid 24 is Ser and amino acid 25 is Gln (1222-5, amino acids 24–34 of SEQ ID NO:6) or in which amino acid 24 is Arg and amino acid 25 is Leu (158-9 amino acids 24–34 of SEQ ID NO:8). More preferred is the hypervariable region lCDR1 in which Y is Ser and Z is Gln (as in amino acids 24–34 of SEQ ID NO:6).

Unless otherwise indicated, any polypeptide chain is hereinafter described as having an amino acid sequence starting at the N-terminal extremity and ending at the C-terminal extremity.

When the antigen binding site comprises both the first and second domains, these may be located on the same polypeptide molecule or, preferably, each domain may be on a different chain, the first domain being part of an immunoglobulin heavy chain or fragment thereof and the second domain being part of an immunoglobulin light chain or fragment thereof.

By "LPS binding molecule" is meant any molecule capable of binding to LPS. The binding reaction may be shown by standard methods (qualitative assays) such as an ELISA using purified LPS or heat treated bacteria or a Western blotting using purified LPS; with reference to a negative control test in which an antigen of unrelated origin, e.g. bovine serum albumin (BSA), is used. A complete description of the assays cited above is given below.

1. Detection of binding to purified LPS in an ELISA

Microtitre plates (flat bottomed; microtest III flexible assay plates: Becton Dickinson, Falcon 3912) are coated with purified LPS at 2 µg/ml in coating buffer (diethylenebarbituric acid-Na salt 30 mM. Na acetate 30 mM, NaCl 116 mM; pH 4.5). 50 µl aliquots of the LPS solution are distributed into each well. Unrelated protein (BSA, 2% in PBS pH 7.2/0.02% sodium azide) is used to determine non-specific binding. Plates are incubated for 1 hr at 37° C. and then overnight at 4° C. in a humidified chamber. Plates are washed 4 times with a washing solution i.e. phosphate buffered saline (PBS) pH 7.2, 0.05% vol/vol Tween 20, 0.02% sodium azide. Plates are blocked with 250 µl/well of 2% BSA in PBS/sodium azide 0.02% for 3 hrs at room temperature. Plates are washed again.

Antibody solutions are prepared in PBS/BSA 2%/sodium azide 0.02% at various dilutions, e.g. 1 µg/ml, 100 ng/ml, 10 ng/ml and 1 ng/ml. 50 µl aliquots of these solutions are distributed in the wells of the precoated plates. Incubation is carried out overnight at room temperature. After 4 washes, 50 µl per well of biotinylated affinity purified goat anti-mouse IgG or IgM of the correct subclass specificity, e.g. anti-mouse IgG2a for WN1 222-5 and anti-mouse IgG2b for WN1 58-9 or anti-human IgG1 or IgM for a variation of WN1 222-5 $_{(huIgM)}$ or WN1 222-5$_{(huIgG1)}$ (final dilution 1/10'000 in PBS 2% BSA; Southern Biotechnology Associates) is added. Incubation is carried out for 4 hrs at room temperature. After 4 washes, 50 µl per well of streptavidin alkaline phosphatase conjugate (Jackson Immuno Research Laboratories; final dilution 1/10'000 in PBS, 2% BSA) is added: Incubation is carried out for 1 hr at room temperature. After 4 washes, 100 µl per well of paranitrophenol phosphate (PNPP) diluted at 1 mg/ml in diethanolamine buffer (diethanolamine 1M, MgCl$_2$.6H$_2$O 0.5 mM, pH 9.8) is added. After 1 hr, absorbance is read at 405 nm using a Titertek Multiskan ELISA reader (MCC/340, Flowlabs).

Advantageously, the purified LPS which is used is selected from smooth, complete core, Rb or Rc LPS. Examples of smooth LPS are LPS extracted from *E. coli* 0111B4 (Difco), *E. coli* 0127B8 (Difco), *E. coli* 0128B12 (Difco), *Salmonella typhimurium* BO ag 0:4, 5, 12 (SH 4809) (Bio-carb). Suitable complete core LPS, Rb LPS and Rc LPS are respectively obtained from *S. Minnesota* (List) and *S. typhimurium* SL 684 (Sigma).

Tables IIA, IIB, IIC, and IID show in tabular form the binding of antibodies WN1 222-5, WN1 58-9, H1 61-2 and SZ27 19.16.07 respectively to purified LPS from different strains of Gram-negative bacteria.

2. Detection of binding to heat killed bacteria

Precoated plates are prepared as described in 1. above, using heat killed bacteria (0.5×10$^8$ cells/ml) rather than purified LPS. The binding reaction is tested and detected as described in 1. above.

Advantageously, the bacteria are smooth wild type bacteria or rough Ra, Rb or Rc mutants.

Tables IIIA, IIIB, IIIC, and IIID show in tabular form the binding of antibodies WN1 222-5, WN1 58-9, H1 61-2 and SZ27 19.16.07 respectively to heat killed bacteria of various Gram-negative strains.

The bacteria listed in Tables II and III are mostly common clinical isolates. The bacteria and/or the corresponding LPS are commercially available or are available on request from Dr. I. Poxton, Dept. of Bacteriology, University of Edinburgh, Scotland, or from Dr H. Brade. Forschungsinstitut Borstel, Borstel, W. Germany.

As will be seen from Tables II and III, the minimum core structure required for recognition by the antibodies of the invention is Rc.

3. Detection of binding to LPS using Western blotting

10 µl aliquots of a LPS solution at 1 mg/ml are mixed with an equal volume of 0.1M Tris-HCl buffer, pH 6.8 containing 1% (wt/vol) sodium deoxycholate (DOC), 20% (wt/vol) glycerin and 0.001% bromophenol blue, and then sonicated. The samples so prepared are loaded onto an electrophoresis gel (4% stacking gel; 14% running gel). The electrophoresis system which is used is a modified Laemmli system (DOC-PAGE; Komuro et al Chem. Pharm. Bull. (1988) 36: 1218) using a Mini Protean II dual slab cell apparatus (Bio Rad Laboratories). The samples are run at a current of 18 mA until the indicator dye enters the separating gel. The current is then increased to 25 mA.

Blotting of the gel is carried out using a 0.45 µm pore size nitrocellulose membrane (Bio Rad Laboratories) and a transfer electrophoresis cell (Mini transblot electrophoretic transfer cell apparatus, Bio Rad Laboratories) at 60 V for 20 min. The blot is soaked in Tris buffer saline (TBS: 20 nM Tris-HCl, 0.1 mM NaCl; pH 7.5) 1% BSA for 1 hr at room temperature. The immunoblot is developed for 2 hrs at room temperature using an antibody preparation at 0.1 µg/ml in TTBS (TBS, 0.05% Tween 20) 1% BSA.

The blot is washed twice in TTBS and further incubated for 45 min at room temperature with a biotinylated goat anti-mouse IgG2a or IgG2b antibody (Southern Biotechnology associates) at a final dilution of 1/10'000 in TTBS, 1% BSA. After washing twice, streptavidin alkaline phosphatase conjugate (Jackson Immuno Research Laboratories), used at a dilution of 1/10'000 in TTBS/BSA 1%, is added. Incubation is carried out for 45 min at room temperature. After 3 washes, the BCIP/NBT alkaline phosphatase colour development solution is added as indicated by the manufacturer (Bio Rad Laboratories). In parallel, the gel is fixed by overnight incubation in a solution containing 40% ethanol and 5% acetic acid and is silver-stained according to the method of Tsai and Frash. Ann. Biochem. (1982) 119: 115.

In this assay, the antibodies of the invention show a binding reaction with LPS extracted either from smooth bacteria or from rough mutants. Particular experiments involving WN1 222-5, WN1 58-9, H1 61-2 and SZ27 19.16.07 are to be seen in FIGS. 4A; 4B, 4C and 4D respectively. The LPS content extracted from a smooth bacterium is separated by electrophoresis into bands corresponding to LPS molecules having different molecular weights, depending on the size of the O-specific side chain. These LPS molecules range from LPS molecules without any O-specific side chain to LPS molecules having 40 or more units in the side chain. The antibodies of the invention react with rough repeating units and all these LPS molecules, containing O-side chain repeating units. This indicates that the epitope for which the LPS-binding molecules of the invention are specific is not hindered by the O-specific side chain. Therefore the majority of LPS molecules of a smooth bacterium are able to react with an LPS-binding molecule of the invention.

Examples of antigen binding molecules include immunoglobulin (Ig) molecules, e.g. antibodies as produced by B-cells or hybridomas and chimeric or humanized antibodies or fragments thereof, e.g. F(ab')$_2$ and Fab fragments, as well as single chain or single domain antibodies. Immunoglobulin molecules may be of different isotypes, for example IgG, IgM, IgA or IgE antibodies, of which IgG are preferred.

A single chain antibody consists of the variable domains of the antibody heavy and light chains of an Ig molecule covalently bound by a peptide linker usually consisting of from 10 to 30 amino acids, preferably from 15 to 25 amino acids. Therefore, such a structure does not include the constant part of the heavy and light chains and it is believed that the small peptide spacer is less antigenic than a whole constant part. By "chimeric antibody" is meant an antibody in which the constant regions of the heavy or light chain or both are of human origin while the variable domains of both heavy and light chains are of non-human (e.g. murine) origin. By "humanized antibody" is meant an antibody in which the hypervariable regions are of non-human (e.g. murine) origin, while all other parts of the immunoglobulin molecule, i.e. the constant regions and the highly conserved framework regions of the variable domains, are of human origin.

Hypervariable regions may be associated with any kind of framework regions, preferably of murine or human origin. Suitable framework regions are described in "Sequences of proteins of immunological interest". Kabat E. A. et al. US department of health and human services. Public health service, National institute of health. However, the preferred framework regions are those of WN1 222-5 or WN1 58-9, wherein the regions of WN1 222-5 are the most preferred.

Sequence Identifier No. 1 shows the complete amino acid sequence of the heavy chain variable domain of WN1 222-5(SEQ ID NO:2), which consists, in sequence from the N-terminal, of framework regions hFR1, hFR2, hFR3 and hFR4 (amino acid positions 1–30, 36–49, 68–100 and 110–120 respectively) interspersed with the hypervariable regions hCDR1, hCDR2 and hCDR3 (amino acid positions 31–35, 50–67, and 101–109 respectively),. In hCDR2 of WN1 222-5 amino acid 54 is Lys and X stands for Lys. Sequence Identifier No. 2 shows the complete amino acid sequence of the heavy chain variable domain of WN1 58-9(SEQ ID NO:4), which consists, in sequence from the N-terminal, of framework regions $hFR1_r$; $hFR2_r$; $hFR3_r$ and hFR4 (amino acid positions 1–30; 36–49; 68–100 and 110–120 respectively) interspersed with the hypervariable regions hCDR1; hCDR2 and hCDR3 (amino acid positions 31–35, 50–67 and 101–109 respectively). In hCDR2 of WN1 58-9 amino acid 54 is Tyr and amino acid 54 is Arg. The index r after the FR stands for an amino acid sequence nearly identical to the amino acid sequence without index. The sequence with index comprises at least one replaced amino acid in contrast to the sequence without index.

Sequence Identifier No. 3 shows the complete amino acid sequence of the light chain variable domain of WN1 222-5 (SEQ ID NO:6), consisting in sequence of framework regions lFR1; lFR2; lFR3 and lFR4 (amino acid positions 1–23; 35–49; 57–88 and 98–107 respectively) interspersed with the hyper-variable regions lCDR1; lCDR2 and lCDR3 (amino acid positions 24–34, 50–56 and 89–97 respectively). In lCDR1 of WN1 222-5 amino acid 26 is Ser and amino acid 27 is stands for Gln. Sequence Identifier No. 4 shows the complete amino acid sequence of the light chain variable domain of WN1 58-9(SEQ ID NO:8), consisting in sequence of framework regions $lFR1_r$; $lFR2_r$; $lFR3_r$ and lFR4 (amino acid positions 1–23, 35–49; 57–88 and 98–107 respectively) interspersed with the hypervariable regions lCDR1, lCDR2 and lCDR3 (amino acid positions 24–34; 50–56 and 89–97 respectively). In lCDR1 of WN1 58-9 (amino acid 26 stands for Arg and amino acid 27 is stands for Leu.

The preferred heavy chain framework is hFR1; hFR2; hFR3 and hFR4 (amino acid positions 1–30, 36–49, 68–100 and 110–120 respectively) as shown in SEQ ID NO:2 and the preferred light chain framework is lFR1; lFR2; lFR3 and lFR4 (amino acid positions 1–23; 35–49; 57–88 and 98–107 respectively) as shown in SEQ ID NO:6.

Accordingly, the invention also provides an LPS binding molecule which comprises at least one antigen binding site comprising either a domain having an amino acid sequence substantially identical to that shown in SEQ ID NO:2 or alternatively SEQ ID NO:4 starting with amino acid at position 1 and ending with amino acid at position 120; or a first domain as described above and a second domain having an amino acid sequence substantially identical to that shown in SEQ ID NO:6 or alternatively SEQ ID NO:8, starting with amino acid at position 1 and ending with amino acid at position 107.

Monoclonal antibodies raised against a toxic antigen must necessarily be developed in a non-human system e.g. in mice. As a direct consequence of this, a xenogenic antibody as produced by a hybridoma, when administered to humans, elicits an undesirable immune response which is essentially mediated by the constant part of the xenogenic immunoglobulin. This clearly limits the use of such antibodies as they cannot be administered over a prolonged period of time. Therefore it is particularly preferred to use single chain antibodies or chimeric or humanized monoclonal antibodies which are less likely to elicit a substantial allogenic response when administered to humans.

In view of the foregoing, a more preferred LPS binding molecule of the invention is selected from a chimeric anti-LPS antibody which comprises at least a) one immunoglobulin heavy chain or fragment thereof which comprises
   (i) a variable domain comprising in sequence the hypervariable regions hCDR1, hCDR2 and hCDR3 (amino acid positions 31–35, 50–67, and 101–109 respectively) as shown in SEQ ID NO:2 or SEQ ID NO:4 and
   (ii) the constant part or fragment thereof of a human heavy chain; and,
b) one immunogiobulin light chain or fragment thereof which comprises
   (i) a variable domain comprising in sequence the hypervariable regions lCDR1; lCDR2 and (amino acid positions 24–34, 50–56 and 89–97 respectively) as shown in SEQ ID NO:6 or SEQ ID NO:8 and
   (ii) the constant part or fragment thereof of a human light chain;

and direct equivalents thereof.

Alternatively, a LPS binding molecule of the invention may be selected from a single chain binding molecule which comprises an antigen binding site comprising a) a first domain comprising in sequence the hypervariable regions hCDR1, hCDR2 and hCDR3 (amino acid positions 31–35, 50–67, and 101–109 respectively) as shown in SEQ ID NO:2 or SEQ ID NO:4.
b) A second domain comprising in sequence the hypervariable regions lCDR1, lCDR2 and lCDR3 (amino acid positions 24–34, 50–56 and 89–97 respectively) as shown in SEQ ID NO:6 or SEQ ID NO:8 and
c) a peptide linker which is bound either to the N-terminal extremity of the first domain and to the C-terminal extremity of the second domain or to the C-terminal extremity of the first domain and to the N-terminal extremity of second domain;

and direct equivalents thereof.

As is well known, minor changes in an amino acid sequence such as deletion, addition or substitution of one or several amino acids may lead to an allelic form of the original protein which has substantially identical properties. Thus, by the term "direct equivalents thereof" is meant either any single domain LPS binding molecule (molecule X)

(i) in which the hypervariable regions taken as a whole are at least 80% homologous, preferably at least 90% homologous, more preferably at least 95% homologous to the hypervariable regions hCDR1, hCDR2 and hCDR3 (amino acid positions 31–35, 50–67, and 101–109 respectively) as shown in SEQ ID NO:2 or SEQ ID NO:4 and, (ii) which is capable of binding to LPS substantially to the same extent as a reference molecule having framework regions identical to those of molecule amino acid 67 is but having hypervariable regions hCDR1, hCDR2 and hCDR3 (amino acid positions 31–35, 50–67, and 101–109 respectively) identical to those shown in SEQ ID NO:2 or SEQ ID NO:4 or any LPS binding molecule having at least two domains per binding site (molecule X')

(i) in which the hypervariable regions taken as a whole are at least 80% homologous, preferably at least 90% homologous, more preferably at least 95% homologous to the hypervariable regions hCDR1, hCDR2, hCDR3, lCDR1, lCDR2 and lCDR3 (amino acid positions 31–35, 50–67, 101–109, 24–34, 50–56 and 89–97 respectively) as shown in SEQ ID NO:2; SEQ ID NO:4; SEQ ID NO:6 and SEQ ID NO:8 and (ii) which is capable of binding to LPS substantially to the same extent as a reference molecule having framework regions and constant parts identical to molecule X' but having hypervariable regions hCDR1, hCDR2, hCDR3, lCDR1, lCDR2 and lCDR3 (amino acid positions 31–35, 50–67, 101–109, 24–34, 50–56 and 89–97 respectively) identical to those shown in SEQ ID NO:2; SEQ ID NO:4; SEQ ID NO:6 and SEQ ID NO:8.

One LPS binding molecule may be considered as binding to LPS substantially to the same extent as another if the two molecules can be shown effectively to compete with each other in competitive ELISA binding assays on different LPS molecules, for example on the LPS from *E. coli* J5 and from Salmonella Ra 60 and if the binding affinities of the two molecules vary from each other in each case by a factor of not more than 100, preferably not more than 10.

Most preferably, the chimeric anti-LPS antibody comprises at least a) one heavy chain which comprises a variable domain having an amino acid sequence substantially identical to that shown in SEQ ID NO:2 starting with amino acid at position 1 and ending with amino acid at position 120 and the constant part of a human heavy chain; and b) one light chain which comprises a variable domain having an amino acid sequence substantially identical to that shown in SEQ ID NO:6 starting with amino acid at position 1 and ending with amino acid at position 107 and the constant part of a human light chain.

The constant part of a human heavy chain may be of the $\gamma_1$, $\gamma_2$, $\gamma_3$, $\gamma_4$, $\mu$, $\alpha_1$, $\alpha_2$, $\delta$ or $\epsilon$ type, preferably of the $\gamma$ type, more preferably of the $\gamma_1$ type, whereas the constant part of a human light chain may be of the $\kappa$ or $\lambda$ type, preferably of the $\kappa$ type. The amino acid sequence of all these constant parts are given in Kabat et al. (supra).

Conjugates of the LPS binding molecules of the invention. e.g. enzyme or toxin conjugates, are also included within the scope of the invention, as are LPS binding molecules labelled with radioactive isotopes or fluorescent markers.

A LPS binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided (i) DNA molecules encoding a single domain LPS binding molecule of the invention, a single chain LPS binding molecule of the invention, a heavy or light chain or fragment thereof of a LPS binding molecule of the invention and (ii) the use of the DNA molecules of the invention for the production of a LPS binding molecule of the invention by recombinant means.

The present state of the art is such that the skilled man will be able to synthetize the DNA molecules of the invention given the information provided herein i.e. the amino acid sequences of the hypervariable regions and the DNA sequences coding for them. A method for constructing a variable domain gene is for example described in EPA 239 400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. Double stranded synthetic CDR cassettes are prepared by DNA synthesis according to the sequences given in SEQ ID NO:2; SEQ ID NO:4; SEQ ID NO:6 or SEQ ID NO:8. These cassettes are provided with sticky ends so that they can be ligated at the junctions of the framework. A protocol for achieving a DNA molecule encoding an immunoglobulin variable domain is shown in FIG. 5.

Furthermore, it is not necessary to have access to the mRNA from a producing hybridoma cell line in order to obtain a DNA construct coding for the MAbs of the invention. Thus PCT application WO 90/07861 gives full instructions for the production of a MAb by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter and genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In view of the foregoing and since the mouse MAb as naturally secreted by the hybridoma is not the preferred type of MAb, it is considered that, although no deposit has been made of the hybridoma producing WN1 222-5 or WN1 58-9, nevertheless the present application discloses the invention in a manner sufficiently clear and complete for it to be carried out by a person skilled in the art.

In a particular embodiment of the invention, the recombinant means for the production of a LPS binding molecule includes first and second DNA constructs as described below:

The first DNA construct encodes a heavy chain or fragment thereof and comprises a) a first part which encodes a variable domain comprising alternately framework and hypervariable regions, said hypervariable regions being in sequence hCDR1, hCDR2 and hCDR3 (amino acid positions 31–35, 50–67, and 101∩respectively) the amino acid sequences of which are shown in SEQ ID NO:2 or SEQ ID NO:4; this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a non-sense codon.

Preferably, this first part encodes a variable domain having an amino acid sequence substantially identical to the amino acid sequence as shown in SEQ ID NO:2 or SEQ ID NO:4 starting with the amino acid at position 1 and ending with the amino acid at position 120. More preferably the first part has the nucleotide sequence as shown in SEQ ID NO:2 or SEQ ID NO:4 starting with the nucleotide at position 1 and ending with the nucleotide at position 361. Also preferably, the second part encodes the constant part of a human heavy chain, more preferably the constant part of the human γ1 chain. This second part may be a DNA fragment of genomic origin (comprising introns) or a cDNA fragment (without introns). The sequence of Sequence Identifier 1 is more preferred than the sequence of Sequence Identifier No.2.

The second DNA construct encodes a light chain or fragment thereof and comprises
a) a first part which encodes a variable domain comprising alternately framework and hypervariable regions; said hypervariable regions being in sequence lCDR1, lCDR2 and lCDR3 (amino acid positions 24–34, 50–56 and 89–97 respectively), the amino acid sequences of which are shown in SEQ ID NO:6 or SEQ ID NO:8; this first part starting with a codon encoding the first amino acid of the variable domain and ending with a codon encoding the last amino acid of the variable domain, and
b) a second part encoding a light chain constant part or fragment thereof which starts with a codon encoding the first amino acid of the constant part of the light chain and ends with a codon encoding the last amino acid of the constant part or fragment thereof followed by a non-sense codon.

Preferably, this first part encodes a variable domain having an amino acid sequence substantially identical to the amino acid sequence as shown in SEQ ID NO:6 or SEQ ID NO:8 starting with the amino acid at position 1 and ending with the amino acid at position 107. More preferably, the first part has the nucleotide sequence as shown in SEQ ID NO:5 or SEQ ID NO:7 starting with the nucleotide at position 1 and ending with the nucleotide at position 322 and 321 respectively . Also preferably the second part encodes the constant part of a human light chain, more preferably the constant part of the human κ chain.

In the first and second DNA constructs, the first and second parts are preferably separated by an intron. In the intron located between the first and second part, an enhancer is preferably inserted. The presence of this genetic element, which is transcribed but not translated, may be required for an efficient transcription of the second part. More preferably the first and second DNA constructs comprise the enhancer of a heavy chain gene.

The first or second DNA construct advantageously comprises a third part which is located upstream of the first part and which encodes a leader peptide. This peptide is required for secretion of the chains by the host organism in which they are expressed and is subsequently removed by the host organism. Preferably, the third part of the first DNA construct encodes a leader peptide of a heavy chain. Also preferably, the third part of the second DNA construct encodes a leader peptide of a light chain. Suitable leader peptides are indicated in Kabat et al. (supra). The structure of genes encoding the heavy and light chain of an Ig molecule is shown diagramatically in FIG. 3A.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal. A suitable transgenic animal may be obtained according to standard methods which include microinjecting the first and second DNA constructs, placed under suitable control sequences. into fertilized ova, transferring the so prepared ova into appropriate pseudo-pregnant females and selecting a descendant expressing the desired antibody.

When the antibody chains are to be produced in a cell culture, the DNA constructs are advantageously inserted together or separately in an expression vector, the latter possibility being preferred. More preferably, they are separately inserted on two different but mutually compatible expression vectors.

Accordingly, the invention also provides an expression vector able to replicate in a prokaryotic or eukaryotic cell line which comprises at least one of the DNA constructs above described.

The next stage is the transfer of the expression vector or vectors containing the DNA constructs into a suitable host organism. When the DNA constructs are separately inserted on two expression vectors, they may be transferred separately, i.e. one type of vector per cell, or co-transferred, this latter possibility being preferred. A suitable host organism may be a bacteria, a yeast or a mammalian cell line, the last of these being preferred. More preferably, the mammalian cell line is of lymphoid origin e.g. a myeloma, hybridoma or a normal immortalized B-cell, but does not express any endogeneous antibody heavy or light chain.

It is also preferred that the host organism contains a large number of copies of the vectors per cell. If the host organism is a mammalian cell line, this desirable goal may be reached by amplifying the number of copies according to standard methods. Amplification methods usually consist of selecting for increased resistance to an antibiotic, said resistance being encoded by the expression vector.

In another aspect of the invention, there is provided a process for producing a multi-chain LPS binding molecule which comprises (i) culturing an organism which has been transformed with the first and second DNA constructs of the invention and (ii) recovering an active LPS binding molecule from the culture.

Alternatively, the heavy and light chains may be separately recovered and reconstituted into an active binding molecule after in vitro refolding. Reconstitution methods are well-known in the art: Examples of methods are in particular provided in EPA 120 674 or in EPA 125 023.

Therefore a process may also comprise
(i) culturing a first organism which is transformed with a first DNA construct of the invention and recovering said heavy chain or fragment thereof from the culture and
(ii) culturing a second organism which is transformed with a second DNA construct of the invention and recovering said light chain or fragment thereof from the culture and
(iii) reconstituting in vitro an active LPS binding molecule from the heavy chain or fragment thereof obtained in (i) and the light chain or fragment thereof obtained in (ii).

In a similar manner, there is also provided a process for producing a single chain or single domain LPS binding molecule which comprises (i) culturing an organism which is transformed with a DNA construct respectively encoding a single chain or single domain LPS binding molecule of the invention and (ii) recovering said molecule from the culture.

In the processes of the invention, it is most preferred that the DNA constructs are inserted into expression vectors.

LPS binding molecules of the invention exhibit very good protective activity against LPS of Gram-negative endotoxemia as shown both in the in vitro IL-6 assay described above, and in the following in vivo bioassay.

Rabbit pyrogen model

Rabbits are weighed and placed in restraining boxes. Probes from the APT 75 (Automatic Pyrogen Test Processor) are inserted in the rectum of each rabbit. The temperature of each rabbit is monitored every 15 minutes from 5 minutes after probe insertion, for an initial period of 95 minutes to establish a base/initial temperature (the base is the mean of the last three readings; if these show a greater than 0.3° range of fluctuation the test is not initialised).

Rabbits are then injected in a marginal ear vein with the LPS-binding molecule followed 30 min to 2 hr later by LPS in the same ear vein. LPS from different *E. coli* and salmonella, e.g. *Salmonella abortus equi* may be used. The suitable dose of LPS-binding molecule is to be determined, depending upon the type of molecule. For example WN1 222-5 is administered at 1 mg to 5 mg per kg body weight. For injection, this antibody is also prepared at 1 mg/ml in pyrogen-free saline and the LPS is injected at 10–100 ng/kg body weight, depending on the LPS used.

Control animals receive either LPS alone or the antibody alone. Rabbits are monitored at 15 min. intervals for a period starting from the injection and not exceeding 300 min.

The percentage of inhibition is measured as follows:

$$\% \text{ inhibition} = 100 - \frac{(\Delta T \text{ for } Ab \text{ and } LPS) - (\Delta T \text{ for } Ab \text{ alone})}{(\Delta T \text{ for } LPS \text{ alone})} \times 100$$

In this assay, LPS binding molecules of the invention significantly reduce the increase of temperature in comparison with the negative control (LPS alone). Depending upon the type of LPS, the % of inhibition may reach levels well above 50%. A protective MAb may be defined in terms of this in vivo assay as one which gives at least 30% inhibition of fever 240 min after an LPS challenge of 10–100 ng/kg With an antibody dose of 1–5 mg/kg.

Therefore the invention also provides
(i) the use of an LPS binding molecule of the invention for preventing or treating gram-negative endotoxemia in humans
(ii) a method of preventing or treating gram-negative endotoxemia in humans which comprises administering an effective amount of an LPS binding molecule of the invention to a patient in need of such treatment.
(iii) a pharmaceutical composition for preventing or treating Gram-negative bacterial infections in humans which comprises an LPS binding molecule of the invention and a pharmaceutically acceptable carrier or diluent.

For these indications, the appropriate dosage will, of course, vary depending upon, for example, the particular molecule of the invention to be employed, the host, the mode of administration and the nature and severity of the condition being treated. However, in therapeutic use, satisfactory results are generally indicated to be obtained by administering at repeated intervals e.g. every two days or twice a week doses of from about 0.1 mg to about 15 mg per kilogram body weight as long as the patient is at risk. A molecule of the invention is conveniently administered parenterally, normally intravenously, for example, into the anticubital or other peripheral vein. A prophylactic treatment typically comprises administering a single dose of a molecule of the invention at a dosage of from about 20 $\mu$g to about 5 mg per Kg body weight.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood or other sugar stabilisers into the saline at the time of formulation. The presence of an excess of such physiologically inert protein prevents loss of monoclonal antibody by adsorption onto the walls of the container and tubing used with the infusion solution. If albumin is used, a suitable concentration is from 0.5 to 4.5% by weight of the saline solution.

LPS binding molecules of the invention, either unlabelled or, preferably, labelled with a radioactive isotope or a fluorescent marker, may also be used for diagnostic purposes to determine the nature, location and extent of Gram-negative bacterial infections, or analytically to detect the presence of LPS or Gram-negative bacterial contamination in water, foodstuffs, biological fluids, etc. Thus for example a labelled LPS binding molecule of the invention may be useful for the imaging of localised infectious foci for surgical removal or other treatment. The LPS binding molecules of the invention may also be attached to a solid phase support-material to form the solid phase of an affinity chromatography purification system for the removal of LPS molecules from biological fluids, e.g. blood serum.

THE FOLLOWING EXAMPLES ILLUSTRATE THE INVENTION

EXAMPLE 1

Figure 1:
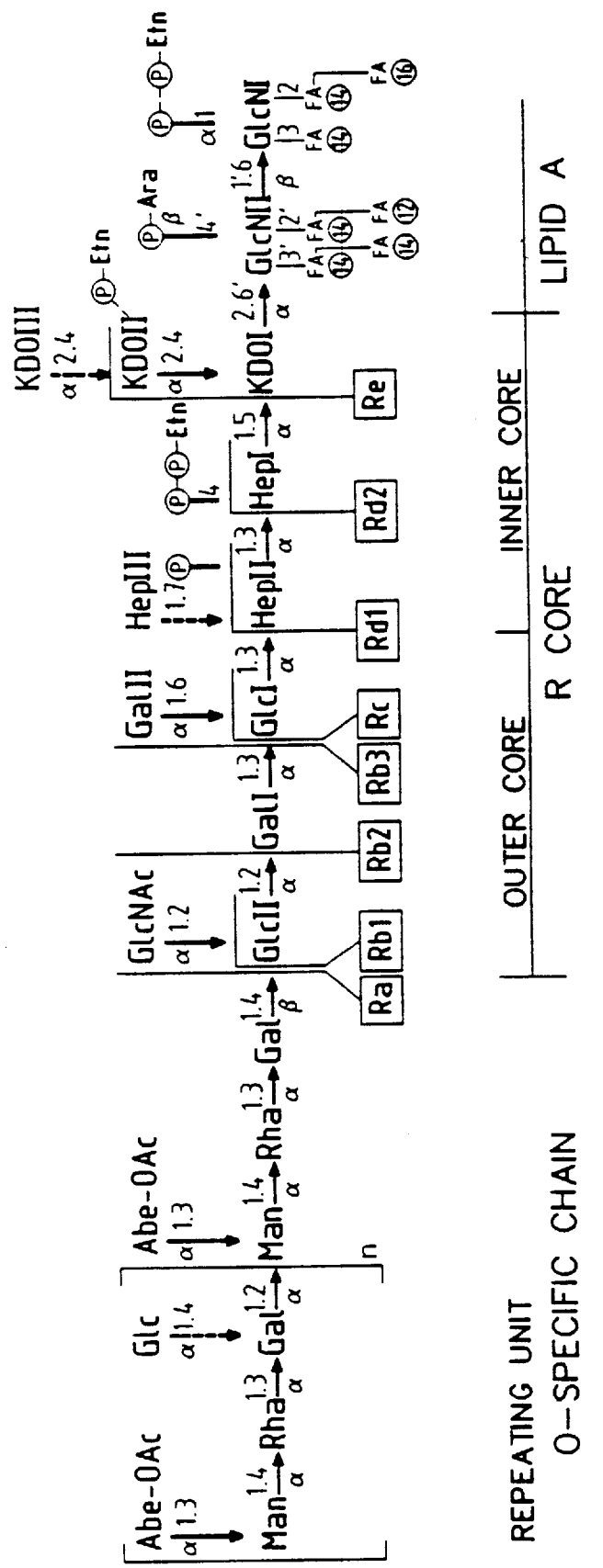
FIG. 1 shows the detailed structure of a Salmonella LPS molecule, indicating the various Ra-Re rough mutant types. In this Figure, Abe=abequose, Ac=acetyl, Ara=4-amino-4-deoxy-L-arabinose. Etn=ethanolamine, FA=hydroxy fatty acid, Gal=D-galactose, Glc=D-glucose, GlcN=D-glucosamine, GlcNAc=N-acetyl-d-glucosamine, Hep= heptose, KDO=2-keto-3-deoxyoctonic acid, Man=mannose, P=phosphate, Rha=L-rhamnose. Dotted lines indicate incomplete substitution.
Figure 2:
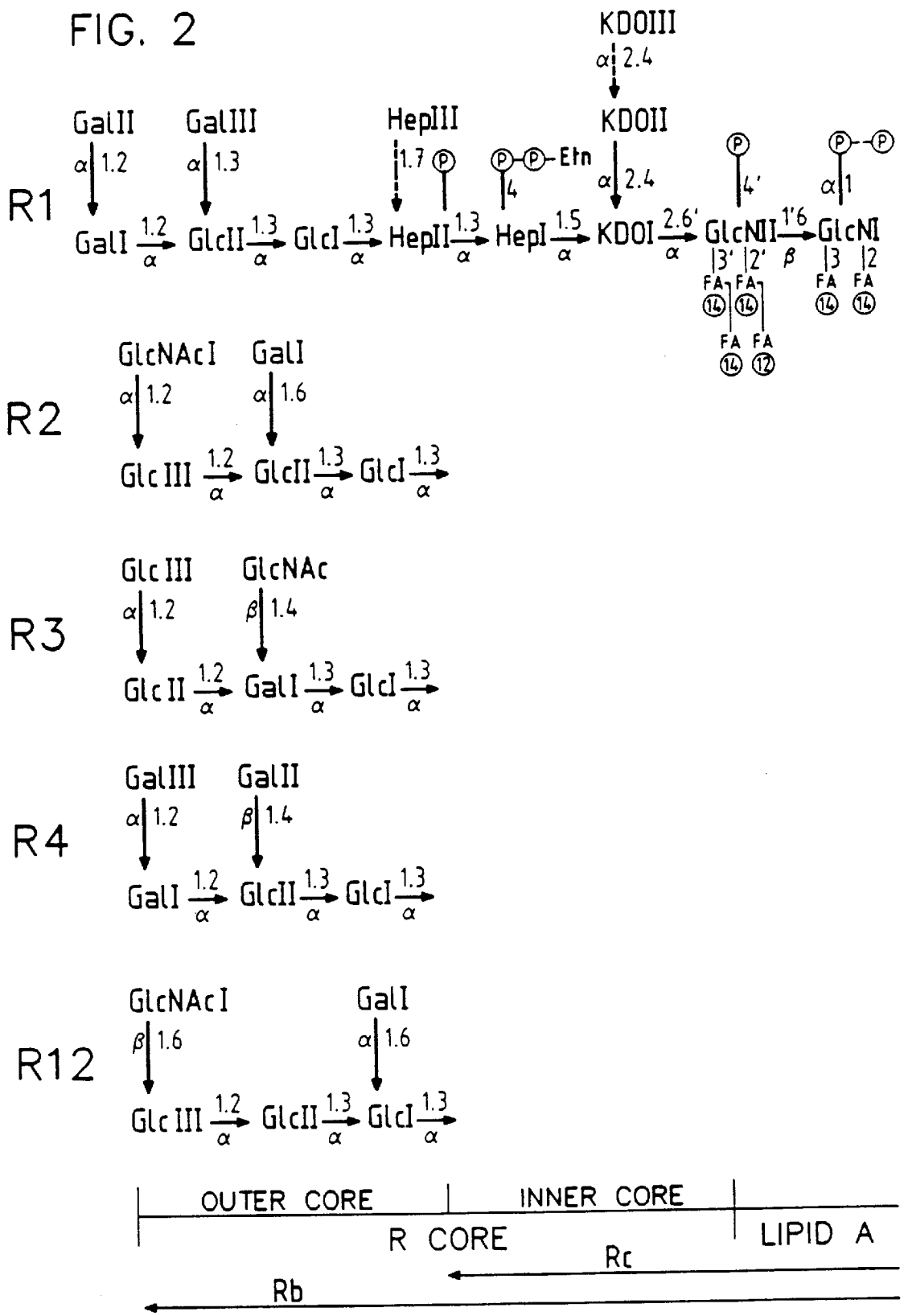
FIG. 2 is a representation of the outer core structures R1; R2; R3; R4 and K12 of different *E. coli* strains. The same abbreviations are used as in FIG. 1.
Figure 3A:
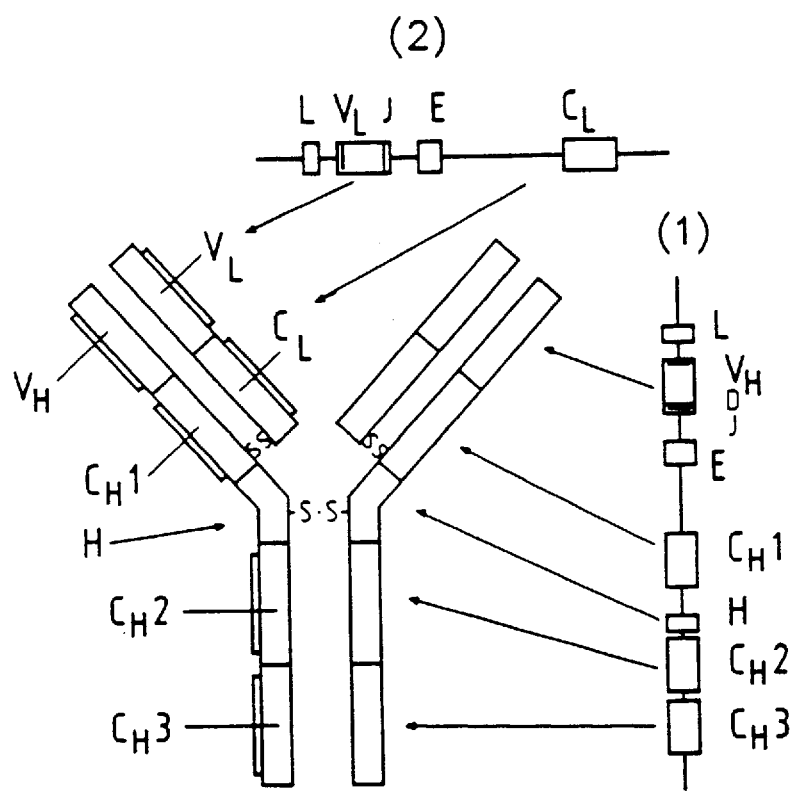
FIG. 3A is a schematic diagram showing the structure of an IgG molecule as well as the genes encoding heavy and light chains respectively designated (1) and (2).
Figure 3B:
FIG. 3B schematically represents the arrangement of a variable domain of a heavy or light chain into framework (FR) and hypervariable (CDR) regions.
Figure 4A:
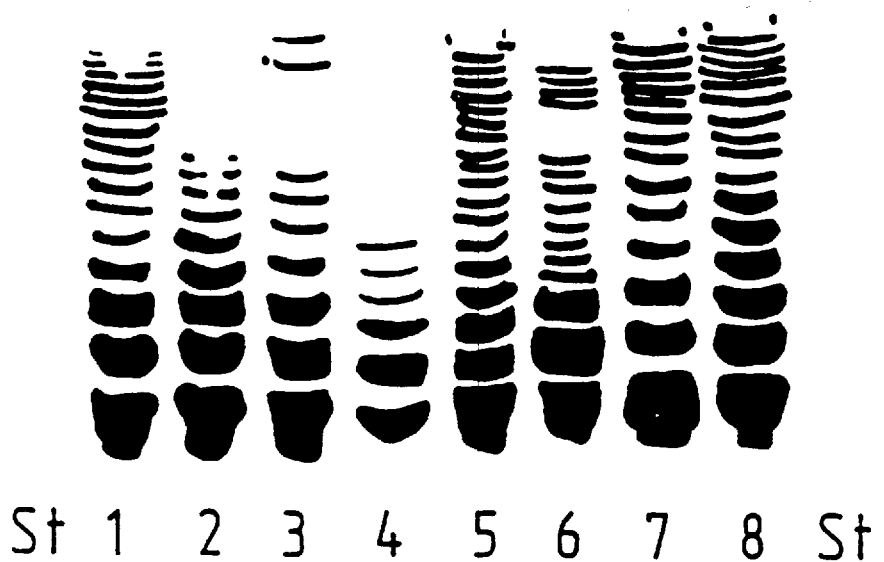
FIG. 4A shows the binding capacity of monoclonal antibody WN1 222-5 against different LPS molecules derived from eight different *E. coli* strains as determined by Western blotting. The drawing represents the spots of the gel. The strains are described in detail in Tables II & III and the lane numbering represents: St=standard; 1=*E. coli* 0111B4; 2=*E. coli* 086; 3=*E. coli* 018K$^-$; 4=*E. coli* 016; 5=*E. coli* 015; 6=*E. coli* 012; 7=*E. coli* 06; and 8=*E. coli* 04.
Figure 4B:
FIG. 4B shows the binding capacity of WN1 58-9 against different LPS molecules derived from eight different bacterial strains as determined by Western blotting. The drawing represents the spots of the gel. The lane numbering represents: St=standard; 1=S. minnesota wild type; 2=E. coli 018; 3=E. coli 016; 4=E. coli 015; 5=E. coli 012; 6=E. coli 06; 7=E. coli 04; and 8=E. coli 02.
Figure 4C:
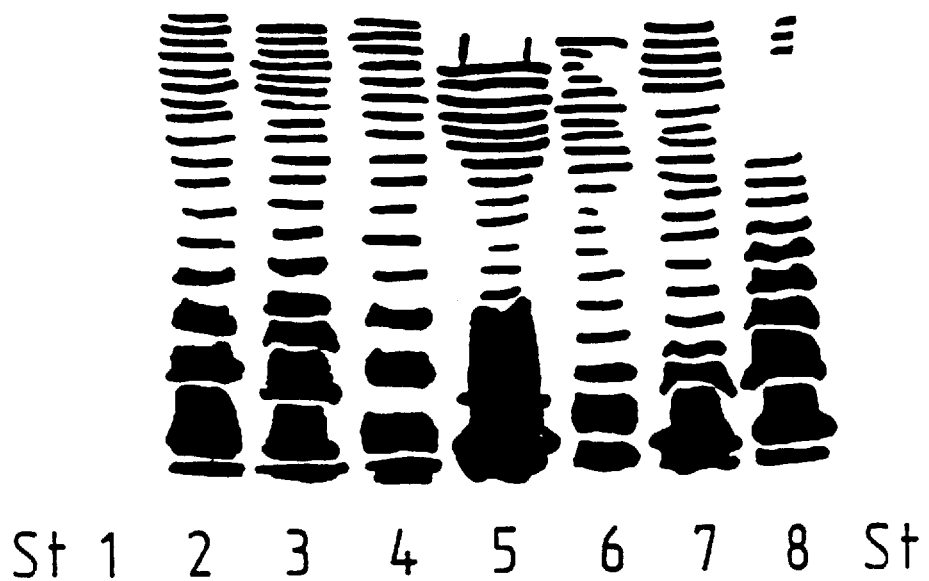
FIG. 4C shows the binding capacity of H1 61-2 against different LPS molecules derived from eight different bacterial strains as determined by Western blotting. The drawing represents the spots of the gel. The lane numbering represents: St=standard; 1=S. minnesota wild type; 2=E. coli 018K⁻; 3=E. coli 04; 4=E. coli 06; 5=E. coli 012; 6=E. coli 015; 7=E. coli 016; and 8=E. coli 086.
Figure 4D:
FIG. 4D shows the binding capacity of SZ27 19.16.07 against different LPS molecules derived from eight different bacterial strains as determined by Western blotting. The drawing represents the spots of the gel. The lane numbering represents: St=standard; 1=E. coli 04; 2=E. coli 016; 3=E. coli 018K⁻; 4=K235; 5=$R_1B$; 6=$R_2B$; 7=$R_3B$ and 8=$R_4B$.
Figure 5:
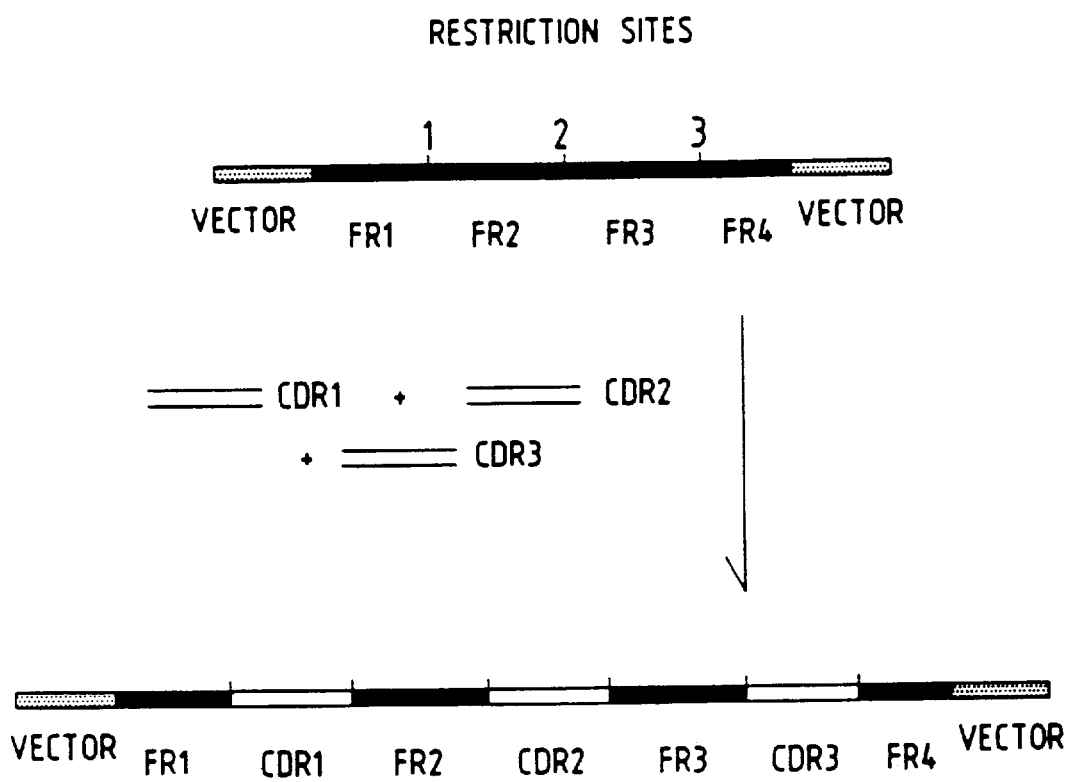
FIG. 5 shows a protocol for constructing CDR replacements by insertion of CDR cassettes into a vector containing 4 framework regions fused together.
Figure 6A:
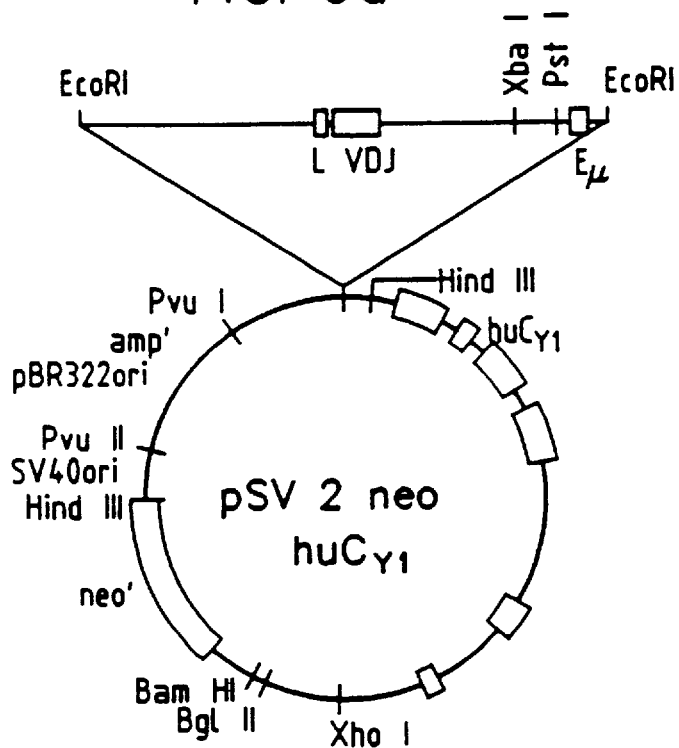
FIGS. 6A and 6B show the parental expression vectors pSV-2 neo and pSV-2DHFR. Both plasmids comprise an ampicillin resistance gene (amp®) and the origin of replication of pBR322 and SV40 (pBR322 ori and SV40 or). pSV-2neo is characterized by the presence of a neomycin gene (neo®) and the gene encoding the human $\gamma_1$ constant part (hu $C\gamma_1$) while pSV-2 DHFR has inserted a dihydrofolate reductase (DHFR) gene (methotrexate resistance) and the gene encoding the human κ constant part (hu $C_\kappa$). The final vectors for expressing the chimeric heavy or light chain are respectively obtained by inserting into pSV-2neo a DNA fragment encoding the leader peptide (L), and the variable domain ($VDJ_4$) of the WN1 222-5 heavy chain together with the mouse heavy chain enhancer and by inserting into pSV2-DHFR a DNA fragment encoding the leader peptide (L) and the variable domain ($VJ_1$) of the WN1 222-5 light chain together with the mouse heavy chain enhancer.
Figure 6B:
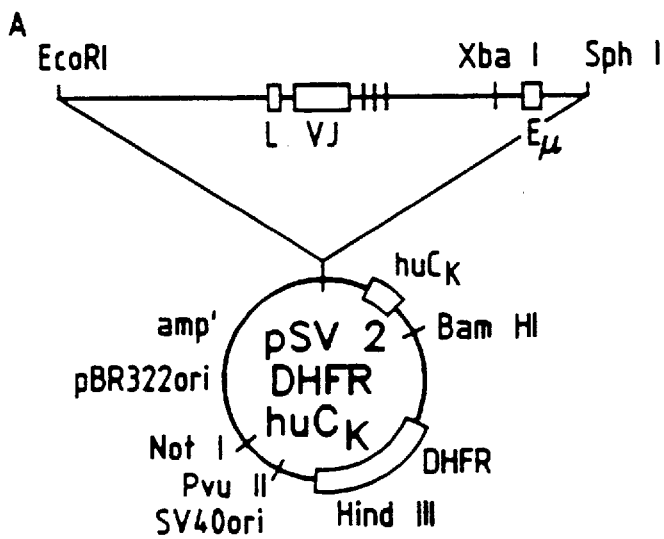
Figure 7:
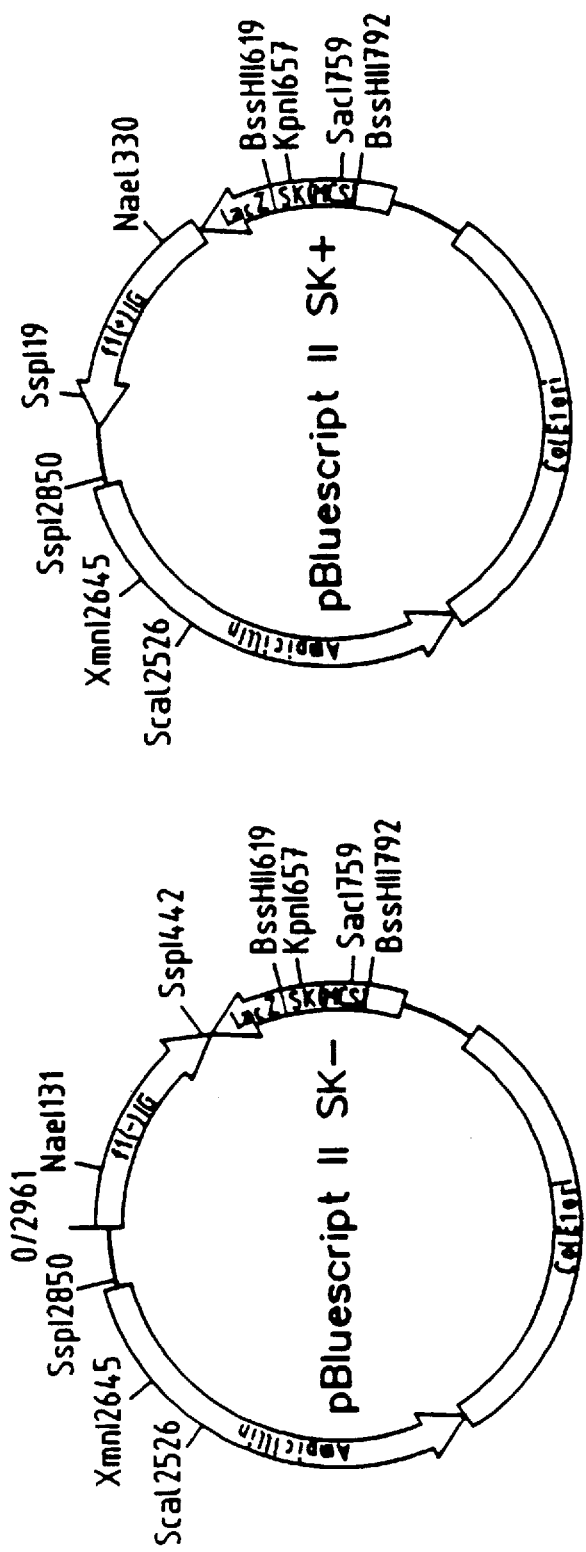
FIG. 7 shows a drawing of the cloning vector p Bluescript II SK⁻ and p Bluescript SK⁺ (Stratagene).

Preparation of Murine Monoclonal Antibody WN1 222-5 a) Immunization Procedure

New Zealand Black mice were immunized i.v. with $10^8$ heat-killed baceria in 0.1 ml. Four injections were carried out, as follows:

week 1 EcR2+EcR3+SmR60
week 2 EcR1+EcR4+Ec018 rough strain
week 3 EcR2+EcR3+SmR60
week 4 EcR1+EcR4+Ec018 rough strain Antibody responses were monitored in tail bleed samples, and a mouse was selected for boosting on the basis of its strong plural response profile.

After one month, two injections, one day apart, of a cocktail of the 6 different strains ($10^8$ heat-killed bacteria) were given, the first injection i.v., the second i.p.

b) Fusion

On the fourth day after boosting, spleen cells were recovered and fused with the non-secreting murine B cell lymphoma PAI-O cell line, using standard procedures. Supernatant from wells containing growing hybridomas were screened using cocktails of different smooth and rough LPS as described above, and hybridomas producing cross-reactive MAb's were cloned.

One of the resulting clones was WN1 222-5, which secretes a murine MAb of the IgG2ak isotype. The WN1 222-5 MAb was purified from culture supernatants collected after in-vitro fermentation of the WN1 222-5 clone and made pyrogen-free by treatment with detergent.

The reactivity pattern of WN1 222-5 is shown in Tables II A and III A.

EXAMPLE 2

Preparation of Murine Monoclonal Antibody WN1 58-9

WN1 58-9 is a further clone obtained from the fusion described in Example 1. Its reactivity pattern is shown in Tables II B and III B.

EXAMPLE 3

Preparation of Murine Monoclonal Antibody H1 61-2

Balb/c mice were immunized i.v. with a cocktail of EcK12, EcR2 and EcR3 ($10^8$ heat-killed bacteria, four injections one week apart). Antibody responses were monitored in tail bleed samples, and a mouse was selected for boosting on the basis of its strong plural response profile.

After one month, two injections, one day apart, of a cocktail of the three different strains ($10^8$ heat-killed bacteria) were given. The first injection was i.v., the second i.p. On the fourth day the spleen cells were fused with the PAI-O cell line using standard procedures.

Primary screening was carried out using the following cocktails of different rough LPS:

1) complete core: EcR2, EcR3, EcK12
2) complete core: EcR1, EcR4, SmR60
3) Rb2: SmR345
4) Rc: EcJ4, St878, SmR5
5) Rd: SmR7, SmR4
6) Re: EcK12, StSL1102, StSL1181, SmR595
7) Lipid A: EcK12, SmR595
8) Negative Control: BSA Hybridomas producing cross-reactive MAb's were cloned, and one of the resulting clones was H1 61-2, which secretes a murine MAb of the IgG1k isotype. The H1 61-2 MAb was purified from culture supernatants. and gave the reactivity pattern shown in Tables IIC and III C.

EXAMPLE 4

Preparation of Murine Monoclonal Antibody SZ 27 19.16.07

Balb/c female mice were immunized with $10^8$ heat-killed bacteria in 0.1 ml i.v. on each of six days (day 0, 1, 2, 7, 8 and 9). Different immunogens were used, at 28 day intervals between starting each immunogen. The immunogens used were

| | |
|---|---|
| 1st 6 injections | P. aeruginosa PAC-605 |
| 2nd 6 injections | EcR1 |

| | |
|---|---|
| 3rd 6 injections | EcR2 |
| 4th 6 injections | EcR3 |

A group of 5 mice received identical immunizations. Antibody responses were monitored in tail bleed samples to purified LPS antigen from the following strains:

S. typh. Ra*, Rb*, Rc*, Rd and Re
S. Minnesota Lipid A

E. coli R1*, C61*, K12, Re (strain D31m4) and Lipid A (ex D31m4)
P. aeruginosa C605*

Strong antibody responses to the marked antigens * had developed after cyclic immunization with 4 different bacteria, and a mouse was selected for boosting on the basis of its strong plural response profile.

Six weeks after completion of the last series of immunization, the selected mouse was boosted i.v. with a cocktail of $2.10^8$ heat-killed bacteria of each of E. coli R1, R2, R3, R4 and K12. The spleen was removed three days later for fusion.

Fusion was carried out with the NS-O cell line using standard procedures.

Primary screening was carried out using two LPS cocktails:
1) S. minnesota Ra+Rc+Re
2) E. coli C62+K12+Re 260 hybridoma supernatants were screened, and 20 of those showing strong responses to both cocktails were selected for further growth. These were then given a secondary screening on 11 different LPS antigens before selection for cloning. These were:

S. typh. Ra, Rb, Rc, Rd and Re
S. minn. Lipid A
E. coli R1, K12, Re, Lipid A
P. aerug. C605.

A number of hybridomas, including SZ27 19 showed the following reaction patterns:
strong S. typh Ra; E. coli R1
weak S. typh Rb, Rc; P. aerug. 602
negative S. typh Rd, Re; E. coli lipid A, K12, Re After subcloning, the clone SZ27 19.16.07 was isolated. It produced a murine MAb of the IgG2ak isotype.

The reaction pattern of this antibody is shown in Tables II D and III D.

EXAMPLE 5

Cloning of the WN1 222-5 or WN1 58-9 heavy chain variable region by Polymerase Chain Reaction (PCR) and construction of a chimeric gene Cloning step No. 1

The amino terminal sequence of the heavy chain is determined as being Glu-Val-Lys-Leu-Val-Glu-Ser-Gly.

Based on this an upstream primer complementary to the mRNA encoding the end of the expected leader sequence and the amino acid sequence cited above is constructed so that its nucleotide sequence reads:

```
          Sal   1
5' AGGT  GTC  GAC  TCC  GAG  GTG  AAG  CTG  GTG  GAG  TCT  GG  3'  (SEQ ID NO: 9)
                        Glu  Val  Lys  Leu  Val  Glu  Ser  Gly
```

A downstream primer complementary to the mRNA encoding a fragment of the mouse γ2a constant part is also constructed so that its nucleotide sequence reads 5' TCCAGGTCAAGGTCACTG 3' (SEQ ID NO:10).

The upstream and downstream primers are used together to amplify a DNA fragment encoding the variable region of the WN1 222-5 heavy chain from a WN1 222-5 mRNA preparation. The amplified DNA fragment is then sequenced and its V, D and J segments are determined.

Cloning Step No. 2

Another downstream primer complementary to the J segment and BstEII having the nucleotide sequence 5' GGAGACGGTGACCGAGGTT 3' (SEQ ID NO:11) is constructed.

To introduce the BstEII restriction site, the original DNA-sequence as naturally found, is slightly modified.

The J-specific downstream primer and the upstream primer already used in the cloning step No. 1 are used to amplify a DNA fragment encoding the variable region of the WN1 222-5 heavy chain from a WN1 222-5 cDNA preparation. The amplification of the WN1 58-9 is made analogously to the one of WN1 222-5. The amplified DNA fragment is further cleaved with Sal I and BstE II and cloned into a heavy chain cassette treated with the same enzyme.

The heavy chain cassette is prepared as follows:

A 2.3 kb EcoRI-SalI DNA fragment comprising the promoter and the leader sequence of the gene encoding the heavy chain of the RFT2 antibody (Heinrich et al, J. of Immunol. (1989) 143: 3589) is cloned into the polylinker region of the cloning vector pBluescript II $SK^-$ (Stratagene). Downstream from this insertion a 0.4 kb BstEII-BamHI DNA fragment comprising the J segment and the beginning of the major intron of the gene encoding an anti-cytomegalovirus antibody (Newkirk et al, J. Clin. Invest. (1988) 81: 1511).

The EcoRI-BamHI fragment is then transferred into pSV2-neo-Eμ-huCγ1 (Heinrich et al; supra) which contains the human heavy chain enhancer (Eμ) and the sequence encoding the human γ1 constant part.

EXAMPLE 6

Cloning of the WN1-222-5 or WN1 58-9 Light Chain Variable Region by PCR and Construction of a Chimeric Gene Cloning steps No. 1 and 2 of Example 5 are repeated using the following primers: Upstream primer:

```
         MluI
5' AGGT ACG CGT TGT GAC ATC CAG ATG AAC CAG TCT CC 3' (SEQ ID NO: 12)
     Thr Arg Cys Val Ile Gln Met Asn Gln Ser Pro
```

Downstream primer specific for the κ constant part:

5' GCACACGACTGAGGCCACCTC 3' (SEQ ID NO: 13)

Downstream primer specific for the J segment

```
             HindIII
5' CGTTTGATTTCAAGCTTGGTG 3' (SEQ ID NO: 14)
```

The amplified DNA fragment is further cleaved with MluI and HindIII and cloned into a light chain cassette treated with the same enzyme. WN1 222-5 and WN1 58-9 are analogously treated.

The light chain cassette is prepared as follows: A 1.3 kb EcoRI-MluI DNA fragment comprising the promoter and the leader sequence of the gene encoding the light chain of the RFT2 antibody (Heinrich et al; Supra) is cloned into the polylinker region of the cloning vector pBluescript II SK⁻ (Stratagene). Downstream from this insertion, a 0.4 kb HindIII-XbaI DNA fragment comprising the J segment and the beginning of the major intron of the gene encoding light chain of RFT2 is cloned.

The EcoRI-XbaI fragment is then transferred into pSV2-DHFR-Eµ-huCκ which is constructed as follows:

A 1.1 kb XbaI—XbaI fragment encoding the murine heavy chain enhancer (Heinrich et al; supra) together with a SphI-HindIII fragment encoding the human κ constant part is subcloned in phage M13 mp18 (Boehringer Mannheim). After disruption of restriction sites by mutagenesis a filled-in EcoRI-HindIII fragment comprising the sequence for the murine heavy chain enhancer (Eµ) and the human κ constant part (huCκ) is cloned in the filled in EcoRI-BamHI site of pSV2-DHFR.

EXAMPLE 7

Expression of a WN1 222-5 or WN1 58-9 chimeric antibody

The expression vectors as obtained in Examples 5 and 6 are co-transferred in a mouse myeloma cell line SP2/O (ATCC CRL 1581) by electroporation using a gene pulser apparatus from Bio Rad Laboratories. This technique is known to create stable transfectants at a high frequency. The SP2/O cell line fails to produce endogeneous heavy and light chains and is sensitive to Gentamycin (G 418) at a concentration of 0.8 mg/l.

SP2/O cells are grown in the usual growth medium (RPMI+10% FCS+5×10⁻⁵ β-mercaptoethanol) harvested in the log phase of growth and washed with the electroporation buffer (Bio-Rad). Cell concentration is adjusted to $2 \times 10^7$ cells/ml. To 0.8 ml of the cell suspension is added 15–20 µg of each plasmid. The mixture is placed on ice and left to stand for 10 min. Then the cells are subjected to an electrical pulse (280 Volt; 25 µF) and again left to stand for 15 min. Cells are transferred to the usual growth medium and incubated at 37° C. in a $CO_2$ incubator.

After 3-day incubation, selection for G 418 resistance is started. Cells are resuspended in fresh medium containing 1.4 mg/ml G 418. The cultures yield growing cells after 10–14 day-incubation in the presence of G 418. After 2-week incubation, the supernatants of the confluent cultures are tested for human IgG expression in a sandwich-type ELISA (anti-human κ-light chain/supernatant/anti-human IgG-alkaline phosphatase conjugate).

This test indicates that complete antibody molecules are secreted in all cultures at varying concentrations in the range of 50–500 ng/ml.

To select cells in which the DHFR gene is amplified and therefore secrete high amounts of the desired antibody two selection procedures for Methotrexate (MTX) resistance are carried out as described below. For this purpose, the G 418 resistant cell pools are each divided and amplification is proceeded either according to procedure A (MTX increase by a factor of 2 or 2.5) or procedure B (MTX increase by a factor of 5).

| G418-resistant Cells | G418-resistant Cells |
|---|---|
| Procedure A | Procedure B |
| 100nM MTX | 200nM MTX |
| 250nM MTX | 1µM MTX |
| 500nM MTX | 5µM MTX |
| 1µM MTX | 25µM MTX |
| 2.5µM MTX | 100µM MTX |
| 5µM MTX | |
| 10µM MTX | |
| 25µM MTX | |
| 100µM MTX | |

Each amplification step comprises inoculating the cells at a density of $2 \times 10^5$ cells/ml in the usual growth medium supplemented with G 418 at 1.4 mg/ml and with MTX at the concentration of choice. After 72 hour incubation, cells and the supernatant separated. Antibody secretion is monitored either by ELISA or by HPLC using a protein A column.

Most of the pools reach a maximum of specific antibody production at a certain MTX concentration. The best producing pools are cloned by limiting dilution. Subsequently, the antibody is purified from a culture supernatant by elution on a protein A affinity column.

SEQUENCE IDENTIFIER No. 1

Subject matter: The immunoglobulin heavy chain variable domain of the WN1 222-5 antibody
Sequence type: Nucleotide sequence (SEQ ID NO:1) and its corresponding amino acid sequence (SEQ ID NO:2)
Length: 361 nucleotides
Original source: A murine hybridoma
Features of the amino acid sequence:

```
hFR1  : from a.a.    1 to  30
hCDR1: from a.a     31 to  35 hFR2  : from a.a.   36 to  49
hCDR2: from a.a.    50 to  67 hFR3  : from a.a.   68 to 100
hCDR3: from a.a.   101 to 109 hFR4  : from a.a.  110 to 120.
```

| | | | | | | | | | | | | | | | | |
|---|---|---|---|---|---|---|---|---|---|---|---|---|---|---|---|---|
| GAG | GTG | AAG | CTG | GTG | GAG | TCT | GGA | GGA | GGC | TTG | GTA | CAG | CCG | GGG | GGT | 48 |
| Glu | Val | Lys | Leu | Val | Glu | Ser | Gly | Gly | Gly | Leu | Val | Gln | Pro | Gly | Gly | |
| | | | | 5 | | | | | 10 | | | | | 15 | | |
| TCT | CTG | AGT | CTC | TCC | TGT | GCA | GCT | TCT | GGA | TTC | ACC | TTC | AGT | GAT | TAC | 96 |
| Ser | Leu | Ser | Leu | Ser | Cys | Ala | Ala | Ser | Gly | Phe | Thr | Phe | Ser | Asp | Tyr | |
| | | | 20 | | | | | 25 | | | | | 30 | | | |
| TAC | ATG | ACC | TGG | GTC | CGC | CAG | GCT | CCA | GGG | AAG | GCA | CCT | GAG | TGG | TTG | 144 |
| Tyr | Met | Thr | Trp | Val | Arg | Gln | Ala | Pro | Gly | Lys | Ala | Pro | Glu | Trp | Leu | |
| | | 35 | | | | | 40 | | | | | 45 | | | | |
| GCT | TTG | ATT | AGA | AAC | AAA | CGT | AAT | GGT | GAC | ACA | GCA | GAG | TAT | AGT | GCA | 192 |
| Ala | Leu | Ile | Arg | Asn | Lys | Arg | Asn | Gly | Asp | Thr | Ala | Glu | Tyr | Ser | Ala | |
| | 50 | | | | | 55 | | | | | 60 | | | | | |
| TCT | GTG | AAG | GGT | CGG | TTC | ACC | ATC | TCC | AGA | GAT | TAT | TCC | CGA | AGC | ATC | 240 |
| Ser | Val | Lys | Gly | Arg | Phe | Thr | Ile | Ser | Arg | Asp | Tyr | Ser | Arg | Ser | Ile | |
| 65 | | | | | 70 | | | | | 75 | | | | | 80 | |
| CTC | CAT | CTT | CAA | ATG | AAT | GCC | CTG | AGA | ACT | GAG | GAC | AGT | GCC | ACT | TAT | 288 |
| Leu | His | Leu | Gln | Met | Asn | Ala | Leu | Arg | Thr | Glu | Asp | Ser | Ala | Thr | Tyr | |
| | | | | 85 | | | | | 90 | | | | | 95 | | |
| TAT | TGT | GTA | AGA | CAG | GGA | CGG | GGC | TAT | ACT | TTG | GAC | TAT | TGG | GGT | CAA | 336 |
| Tyr | Cys | Val | Arg | Gln | Gly | Arg | Gly | Tyr | Thr | Leu | Asp | Tyr | Trp | Gly | Gln | |
| | | | 100 | | | | | 105 | | | | | 110 | | | |
| GGA | ACC | TCA | GTC | ACC | GTC | TCC | TCA | G | | | | | | | | 361 |
| Gly | Thr | Ser | Val | Thr | Val | Ser | Ser | | | | | | | | | |
| | | 115 | | | | 120 | | | | | | | | | | |

SEQUENCE IDENTIFIER No. 2

Subject matter: The immunoglobulin heavy chain variable domain of the WN1 58-9 antibody Sequence type: Nucleotide sequence (SEQ ID NO:3) and its corresponding amino acid sequence (SEQ ID NO:4)
Length: 360 nucleotides
Original source: A murine hybridoma
Features of the amino acid sequence:

```
hFR1ᵣ : from a.a.    1 to  30
hCDR1: from a.a.    31 to  35 hFR2ᵣ : from a.a.   36 to  49
hCDR2: from a.a.    50 to  67 hFR3ᵣ : from a.a.   68 to 100
hCDR3: from a.a.   101 to 109 hFR4  : from a.a.  110 to 120.
```

| | | | | | | | | | | | | | | | | |
|---|---|---|---|---|---|---|---|---|---|---|---|---|---|---|---|---|
| GAG | GTG | AAG | CTG | GTG | GAG | TCT | GGA | GGA | GGC | TTG | GTA | CAG | CCT | GGG | GGT | 48 |
| Glu | Val | Lys | Leu | Val | Glu | Ser | Gly | Gly | Gly | Leu | Val | Gln | Pro | Gly | Gly | |
| | | | | 5 | | | | | 10 | | | | | 15 | | |
| TCT | CTG | CGT | CTC | TCC | TGT | GCA | GCT | TCT | GGA | TTC | ACC | TTC | ATT | GAT | TAC | 96 |
| Ser | Leu | Arg | Leu | Ser | Cys | Ala | Ala | Ser | Gly | Phe | Thr | Phe | Ile | Asp | Tyr | |
| | | | 20 | | | | | 25 | | | | | 30 | | | |
| TAC | ATG | ACC | TGG | GTC | CGC | CAT | CCG | CCA | GGG | GAG | GCA | CCT | GAA | TGG | TTG | 144 |
| Tyr | Met | Thr | Trp | Val | Arg | His | Pro | Pro | Gly | Glu | Ala | Pro | Glu | Trp | Leu | |
| | | 35 | | | | | 40 | | | | | 45 | | | | |
| GCT | TTG | ATT | AGA | AAC | TAC | CGT | AAT | GGT | GAC | ACA | GCA | GAA | TAC | AGT | GCA | 192 |
| Ala | Leu | Ile | Arg | Asn | Tyr | Arg | Asn | Gly | Asp | Thr | Ala | Glu | Tyr | Ser | Ala | |
| | 50 | | | | | 55 | | | | | 60 | | | | | |
| TCT | GTG | AGG | GGT | CGG | TTC | ACC | ATC | TCC | AGA | GAT | GAT | TCC | CAA | AGC | ATC | 240 |
| Ser | Val | Arg | Gly | Arg | Phe | Thr | Ile | Ser | Arg | Asp | Asp | Ser | Gln | Ser | Ile | |
| 65 | | | | | 70 | | | | | 75 | | | | | 80 | |
| CTC | TAT | CTT | CAA | ATG | AAT | GCC | CTG | AGA | GCT | GAG | GAC | AGT | GCC | ACT | TAT | 288 |
| Leu | Tyr | Leu | Gln | Met | Asn | Ala | Leu | Arg | Ala | Glu | Asp | Ser | Ala | Thr | Tyr | |
| | | | | 85 | | | | | 90 | | | | | 95 | | |
| TAC | TGT | GTA | AGA | CAG | GGA | CGG | GGC | TAT | ACT | CTG | GAC | TAT | TGG | GGT | CAA | 336 |
| Tyr | Cys | Val | Arg | Gln | Gly | Arg | Gly | Tyr | Thr | Leu | Asp | Tyr | Trp | Gly | Gln | |
| | | | 100 | | | | | 105 | | | | | 110 | | | |
| GGA | ACC | TCA | GTC | ACC | GTC | TCC | TCA | | | | | | | | | 360 |
| Gly | Thr | Ser | Val | Thr | Val | Ser | Ser | | | | | | | | | |
| | | 115 | | | | 120 | | | | | | | | | | |

SEQUENCE IDENTIFIER No. 3

Subject matter: The immunoglobulin light chain variable domain of the WN1 222-5 antibody
Sequence type: Nucleotide sequence (SEQ ID NO:5) and its corresponding amino acid sequence (SEQ ID NO:6)
Length: 322 nucleotides
Original source: A murine hybridoma
Features of the amino acid sequence:

```
lFR1  : from a.a.    1 to  23
lCDR1: from a.a     24 to  34 lFR2  : from a.a.   35 to  49
lCDR2: from a.a.    50 to  56 lFR3  : from a.a.   57 to  88
lCDR3: from a.a.    89 to  97 lFR4  : from a.a.   98 to 107.
```

DNA and AA sequence

Light Chain:

```
GAC ATC CAG ATG AAC CAG TCT CCA TCC AGT CTG TCT GCA TCC CTC    45
Asp Ile Gln Met Asn Gln Ser Pro Ser Ser Leu Ser Ala Ser Leu
                 5                  10                 15
GGA GAC ACA ATT TCC ATC ACT TGC CGT GCC AGT CAG AAC ATT AAT    90
Gly Asp Thr Ile Ser Ile Thr Cys Arg Ala Ser Gln Asn Ile Asn
                20                  25                 30
ATT TGG TTA AGC TGG TAT CAG CAA AAA CCA GGA AAT GTT CCT AAA   135
Ile Trp Leu Ser Trp Tyr Gln Gln Lys Pro Gly Asn Val Pro Lys
                35                  40                 45
CTT TTA ATC TAT AAG GCT TCC AAC TTG CAC ACA GGC GTC CCA TCA   180
Leu Leu Ile Tyr Lys Ala Ser Asn Leu His Thr Gly Val Pro Ser
                50                  55                 60
AGG TTT AGT GGC AGT GGA TCT GGA ACA GAT TTC ACA TTA ATC ATC   225
Arg Phe Ser Gly Ser Gly Ser Gly Thr Asp Phe Thr Leu Ile Ile
                65                  70                 75
AGC AGT CTG CAG CCT GAA GAC ATT GCC ACT TAC TAC TGT CTA CAG   270
Ser Ser Leu Gln Pro Glu Asp Ile Ala Thr Tyr Tyr Cys Leu Gln
                80                  85                 90
GGT CAA AGT TAT CCT CGT ACG TTC GGT GGA GGC ACC AAG CTG GAG   315
Gly Gln Ser Tyr Pro Arg Thr Phe Gly Gly Gly Thr Lys Leu Glu
                95                 100                105
ATC AAA C                                                      322
Ile Lys
107
```

SEQUENCE IDENTIFIER No. 4

Subject matter: The immunoglobulin light chain variable domain of the WN1 58-9 antibody
Sequence type: Nucleotide sequence (SEQ ID NO:7 and its corresponding amino acid sequence (SEQ ID NO:8
Length: 321 nucleotides
Original source: A murine hybridoma
Features of the amino acid sequence:

```
lFR1_r : from a.a.   1 to  23
lCDR1:  from a.a.   24 to  34 lFR2_r : from a.a.  35 to  49
lCDR2:  from a.a.   50 to  56 lFR3_r : from a.a.  57 to  88
lCDR3:  from a.a.   89 to  97 lFR4  : from a.a.   98 to 107.
```

```
GAC ATC CAG ATG AAC CAG TCT CCA TCC AGT CTG TCT GCA TCC CTC    45
Asp Ile Gln Met Asn Gln Ser Pro Ser Ser Leu Ser Ala Ser Leu
                 5                  10                 15
GGA GAC ACA ATT ACC ATC ACT TGC CGT GCC AGA CTG AAC ATT AAT    90
Gly Asp Thr Ile Thr Ile Thr Cys Arg Ala Arg Leu Asn Ile Asn
                20                  25                 30
```

```
ATT TGG TTA AGT TGG TAC CAG CAG AAA GCA GGA AAT ATT CCT AAA   135
Ile Trp Leu Ser Trp Tyr Gln Gln Lys Ala Gly Asn Ile Pro Lys
                35                      40                  45
CTT TTG ATC TCT AAG GCT TCC AAC TTG CAC ACA GGC GTC CCA TCA   180
Leu Leu Ile Ser Lys Ala Ser Asn Leu His Thr Gly Val Pro Ser
            50                      55                  60
AGG TTT AGT GGC AGT GGA TCT GGA ACA GAT TTC ACA TTA ACC ATC   225
Arg Phe Ser Gly Ser Gly Ser Gly Thr Asp Phe Thr Leu Thr Ile
            65                      70                  75
AGC AGT CTG CGG CCT GAA GAC ATT GCC ACT TAC TAC TGT CTA CAG   270
Ser Ser Leu Arg Pro Glu Asp Ile Ala Thr Tyr Tyr Cys Leu Gln
            80                      85                  90
GGT CAA AGT TAT CCT CGT ACG TTC GGT GGA GGC ACC AAG CTT GAA   315
Gly Gln Ser Tyr Pro Arg Thr Phe Gly Gly Gly Thr Lys Leu Glu
            95                     100                 105
ATC AAA                                                       321
Ile Lys
    107
```

TABLE I

| Region | Location on the heavy chains | Location on the light chains |
|---|---|---|
| FR1/FR1$_r$ | amino acid 1 to 30 | amino acid 1 to 23 |
| CDR1/CDR1 | amino acid 31 to 35 | amino acid 24 to 34 |
| FR2/FR2$_r$ | amino acid 36 to 49 | amino acid 35 to 49 |
| CDR2/CDR2 | amino acid 50 to 67 | amino acid 50 to 56 |
| FR3/FR3$_r$ | amino acid 68 to 100 | amino acid 57 to 88 |
| CDR3 | amino acid 101 to 109 | amino acid 89 to 97 |
| FR4 | amino acid 110 to 120 | amino acid 98 to 107 |

The locations are applicable to SEQ ID NO:2 and SEQ ID NO:4 with respect to the heavy chains, and to SEQ ID NO:6 and SEQ ID NO:8 with respect to the light chains.

TABLE IIA

| CHEMOTYPE | | | | WN1 222-5 | | |
|---|---|---|---|---|---|---|
| mAb | | STRAIN | SUPPLIER | 100 ng/ml | 10 ng/ml | 1 ng/ml |
| LPS | Smooth *E. coli* | 02 | Univ. Edinburgh | +++++ | ++++ | ++ |
| LPS | Smooth *E. coli* | 04 | Univ. Edinburgh | +++++ | +++++ | ++++ |
| LPS | Smooth *E. coli* | 06 | Univ. Edinburgh | +++++ | +++++ | +++ |
| LPS | Smooth *E. coli* | 012 | Univ. Edinburgh | +++++ | +++++ | ++ |
| LPS | Smooth *E. coli* | 015 | Univ. Edinburgh | +++++ | +++++ | ++++ |
| LPS | Smooth *E. coli* | 016 | Univ. Edinburgh | +++++ | +++++ | ++ |
| LPS | Smooth *E. coli* | 018K− | Univ. Edinburgh | +++++ | +++++ | +++ |
| LPS | Smooth *E. coli* | 018K+ | Univ. Edinburgh | +++++ | +++++ | ++++ |
| LPS | Smooth *E. coli* | 026B6 | Difco | +++++ | +++++ | +++ |
| LPS | Smooth *E. coli* | 055B5 | Difco | +++++ | ++ | + |
| LPS | Smooth *E. coli* | 075 | Univ. Edinburgh | +++++ | +++++ | +++ |
| LPS | Smooth *E. coli* | 086 | Univ. Edinburgh | +++++ | +++++ | +++ |
| LPS | Smooth *E. coli* | 0111B4 | Difco | +++++ | +++++ | ++ |
| LPS | Smooth *E. coli* | 0127B8 | Difco | +++++ | +++++ | +++ |
| LPS | Smooth *E. coli* | 0128B12 | Difco | ++++ | +++ | ++ |
| LPS | Smooth *E. coli* | K235 | List | +++++ | +++++ | +++ |
| LPS | Smooth *S. minnesota* | wt | List | +++++ | +++++ | +++ |
| LPS | Smooth *S. typhimurium* | wt | Difco | +++++ | +++++ | ++ |
| LPS | Smooth *S. typhimurium* | B0 ag 0:4,5,12 (SH 4809) | Bio-Carb | +++++ | ++++ | + |
| LPS | Smooth *S. typhimurium* | B0 ag 0:1,4,5,12 (SL 3622) | Bio-Carb | +++++ | ++++ | + |
| LPS | Smooth *S. typhimurium* | B0 ag 0:4,5,12^2 (SH 4305) | Bio-Carb | ++++++ | +++++ | + |
| LPS | Smooth *S. typhi* | D0 ag 0:9,12^2 (253 Ty) | Bio-Carb | +++++ | +++++ | +++ |
| LPS | Smooth *S. newport* | C2 ag 0:6,8 | Bio-Carb | +++++ | +++++ | +++ |
| LPS | Smooth *S. enteridis* | D0 ag 0:9,12 (SH 1262) | Bio-Carb | +++++ | +++++ | +++ |
| LPS | Smooth *S. thompson* | C1 ag 0:6,7, (ls40) | Bio-Carb | +++++ | +++++ | ++++ |
| LPS | Smooth *S. abortus equi* | (H1178) | Institut Borsiel | +++++ | +++++ | ++++ |
| LPS | cCore *E. coli* | K12 | Univ. Edinburgh | +++++ | +++++ | ++ |
| LPS | cCore *E. coli* | C62 | Univ. Edinburgh | ++++ | +++++ | ++ |
| LPS | cCore *E. coli* | R1 | Institut Borstel | +++++ | +++++ | ++ |
| LPS | cCore *E. coli* | R2 | Institut Borstel | +++++ | +++++ | ++ |
| LPS | cCore *E. coli* | R3 | Institut Borstel | +++++ | +++++ | ++++ |
| LPS | cCore *E. coli* | R4 | Institut Borstel | +++++ | +++++ | +++ |
| LPS | cCore *S. minnesota* | Ra R60 | List | +++++ | +++++ | +++ |

TABLE IIA-continued

| CHEMOTYPE | | | | | WN1 222-5 | | |
|---|---|---|---|---|---|---|---|
| mAb | | STRAIN | | SUPPLIER | 100 ng/ml | 10 ng/ml | 1 ng/ml |
| LPS | cCore | S. typhimurium | TV119 | Sigma | +++++ | +++++ | +++ |
| LPS | cCore | S. typhimurium | 1542 | Univ. Edinburgh | +++++ | +++++ | ++++ |
| LPS | cCore | K. aerogenes | M10B | Univ. Edinburgh | − | − | − |
| LPS | Rb2 | S. minnesota | R345 | List | ++++++ | +++++ | ++++ |
| LPS | Rb3 | S. minnesota | | Bio-Carb | ++++++ | +++++ | ++ |
| LPS | Rc | E. coli | J5 | List | ++++++ | +++++ | ++++ |
| LPS | Rc | S. typhimurium | 878 | Univ. Edinburgh | ++++++ | +++++ | ++ |
| LPS | Rc | S. typhimurium | SL684 | Sigma | ++++++ | +++++ | ++++ |
| LPS | Rc | P. aeruginosa | PAC605 | Univ. Edinburgh | + | + | + |
| LPS | RcP− | S. minnesota | R5 | List | ++++++ | +++++ | ++++ |
| LPS | Rd2 | E. coli | F583 | Sigma | ++++++ | +++++ | +++ |
| LPS | Rd1P− | S. minnesota | R7 | List | +++ | ++ | + |
| LPS | Rd2 | S. minnesota | R4 (V594) | Institut Borstel | ++++ | +++ | ++ |
| LPS | Re | E. coli | K12 (D31m4) | List | ++++ | ++++ | ++ |
| LPS | Re | E. coli | F515 | Institut Borstel | +++++ | +++++ | ++++ |
| LPS | Re | S. minnesota | R595 | List | + | + | − |
| LPS | Re | S. typhimurium | SL1102 | Univ. Edinburgh | − | − | − |
| LPS | Re | S. typhimurium | SL1181 | Sigma | − | − | − |
| Lipid A | | E. coli | K12 (ex-D31m4) | List | − | − | − |
| Lipid A | | S. minnesota | R595 | List | − | − | − |
| BSA | | | | | − | − | − |

Purified native LPS (2 ug/ml) were used to coat the plates
Values are reported as O.D., one + equals 0.5 O.D. (405 nm).

TABLE IIB

| CHEMOTYPE | | | | | WN1 58–9 MAb | | |
|---|---|---|---|---|---|---|---|
| | | STRAIN | | SUPPLIER | 100 ng/ml | 10 ng/ml | 1 ng/ml |
| LPS | Smooth | E. coli | 02 | Univ. Edinburgh | ++++ | ++++ | + |
| LPS | Smooth | E. coli | 04 | Univ. Edinburgh | +++++ | ++++ | + |
| LPS | Smooth | E. coli | 06 | Univ. Edinburgh | ++++ | +++++ | − |
| LPS | Smooth | E. coli | 012 | Univ. Edinburgh | ++++ | +++++ | + |
| LPS | Smooth | E. coli | 015 | Univ. Edinburgh | +++++ | +++++ | ++ |
| LPS | Smooth | E. coli | 016 | Univ. Edinburgh | ++++ | +++++ | + |
| LPS | Smooth | E. coli | 018K− | Univ. Edinburgh | ++++ | ++++ | + |
| LPS | Smooth | E. coli | 018K+ | Univ. Edinburgh | +++++ | +++++ | ++ |
| LPS | Smooth | E. coli | 026B6 | Difco | +++++ | +++++ | + |
| LPS | Smooth | E. coli | 055B5 | Difco | +++ | + | − |
| LPS | Smooth | E. coli | 075 | Univ. Edinburgh | ++++ | ++ | − |
| LPS | Smooth | E. coli | 086 | Univ. Edinburgh | ++++ | ++++ | + |
| LPS | Smooth | E. coli | 0111B4 | Difco | ++++ | ++++ | + |
| LPS | Smooth | E. coli | 0127B8 | Difco | ++++ | +++ | + |
| LPS | Smooth | E. coli | 0128B12 | Difco | ++ | ++ | − |
| LPS | Smooth | E. coli | K235 | List | ++++ | ++++ | + |
| LPS | Smooth | S. minnesota | wt | List | ++++ | ++++ | + |
| LPS | Smooth | S. typhimurium | wt | Difco | ++++ | ++++ | + |
| LPS | Smooth | S. typhimurium | B0 ag 0:4,5,12 (SH 4809) | Bio-Carb | ++++ | +++ | − |
| LPS | Smooth | S. typhimurium | B0 ag 0:1,4,5,12 (SL 3622) | Bio-Carb | ++++ | +++ | + |
| LPS | Smooth | S. typhimurium | B0 ag 0:4,5,12^2 (SH 4305) | Bio-Carb | ++++ | ++++ | + |
| LPS | Smooth | S. typhi | D0 ag 0:9,12^2 (253 Ty) | Bio-Carb | +++++ | +++++ | + |
| LPS | Smooth | S. newport | C2 ag 0:6,8 | Bio-Carb | +++++ | +++++ | + |
| LPS | Smooth | S. enteridis | D0 ag 0:9,12 (SH 1262) | Bio-Carb | +++++ | ++++ | + |
| LPS | Smooth | S. thompson | C1 ag 0:6,7, (ls40) | Bio-Carb | +++++ | +++++ | ++ |
| LPS | Smooth | S. abortus equi | (H1178) | Institut Borsiel | +++++ | +++++ | ++ |
| LPS | cCore | E. coli | K12 | Univ. Edinburgh | ++++ | ++++ | + |
| LPS | cCore | E. coli | C62 | Univ. Edinburgh | +++++ | +++++ | +++ |
| LPS | cCore | E. coli | R1 | Institut Borstel | +++++ | +++++ | + |
| LPS | cCore | E. coli | R2 | Institut Borstel | ++++ | +++ | + |
| LPS | cCore | E. coli | R3 | Institut Borstel | +++++ | +++++ | + |
| LPS | cCore | E. coli | R4 | Institut Borstel | ++++ | +++++ | + |
| LPS | cCore | S. minnesota | Ra R60 | List | ++++ | +++++ | + |
| LPS | cCore | S. typhimurium | TV119 | Sigma | ++++ | ++++ | + |
| LPS | cCore | S. typhimurium | 1542 | Univ. Edinburgh | ++++ | +++++ | + |
| LPS | cCore | K. aerogenes | M10B | Univ. Edinburgh | − | − | − |
| LPS | Rb2 | S. minnesota | R345 | List | +++++ | +++++ | +++ |
| LPS | Rb3 | S. minnesota | | Bio-Carb | +++++ | +++++ | + |
| LPS | Rc | E. coli | J5 | List | +++++ | +++++ | + |
| LPS | Rc | S. typhimurium | 878 | Univ. Edinburgh | +++++ | +++++ | + |
| LPS | Rc | S. typhimurium | SL684 | Sigma | +++++ | +++++ | ++ |
| LPS | Rc | P. aeruginosa | PAC605 | Univ. Edinburgh | + | + | − |

TABLE IIB-continued

| CHEMOTYPE | | STRAIN | | SUPPLIER | WN1 58–9 MAb | | |
|---|---|---|---|---|---|---|---|
| | | | | | 100 ng/ml | 10 ng/ml | 1 ng/ml |
| LPS | RcP⁻ | S. minnesota | R5 | List | +++++ | +++++ | ++ |
| LPS | Rd2 | E. coli | F583 | Sigma | +++++ | +++++ | ++ |
| LPS | Rd1P⁻ | S. minnesota | R7 | List | ++++ | ++ | − |
| LPS | Rd2 | S. minnesota | R4 (V594) | Institut Borstel | ++++ | +++ | − |
| LPS | Re | E. coli | K12 (D31m4) | List | +++++ | +++++ | ++ |
| LPS | Re | E. coli | F515 | Institut Borstel | +++++ | +++++ | +++ |
| LPS | Re | S. minnesota | R595 | List | + | − | − |
| LPS | Re | S. typhimurium | SL1102 | Univ. Edinburgh | − | − | − |
| LPS | Re | S. typhimurium | SL1181 | Sigma | − | − | − |
| Lipid A | | E. coli | K12 (ex-D31m4) | List | − | − | − |
| Lipid A | | S. minnesota | R595 | List | − | − | − |
| BSA | | | | | − | − | − |

Purified native LPS (2 μg/ml) were used to coat the plates
Values are reported as O.D., one + equals 0.5 O.D. (405 nm).
BSA = bovine serum albumin

TABLE IIC

| CHEMOTYPE | | STRAIN | | SUPPLIER | HI 61–2 IgG1 | | | |
|---|---|---|---|---|---|---|---|---|
| | | | | | 1 μg/ml | 100 ng/ml | 10 ng/ml | 1 ng/ml |
| LPS | Smooth | E. coli | 02 | Univ. Edinburgh | ++++ | +++++ | ++ | − |
| LPS | Smooth | E. coli | 06 | Univ. Edinburgh | +++ | +++++ | ++ | − |
| LPS | Smooth | E. coli | 012 | Univ. Edinburgh | +++++ | +++++ | +++++ | +++ |
| LPS | Smooth | E. coli | 015 | Univ. Edinburgh | +++++ | +++++ | ++++ | + |
| LPS | Smooth | E. coli | 016 | Univ. Edinburgh | + | ++ | − | − |
| LPS | Smooth | E. coli | 018K− | Univ. Edinburgh | +++++ | +++++ | +++++ | + |
| LPS | Smooth | E. coli | 018K+ | Univ. Edinburgh | +++++ | +++++ | +++++ | ++ |
| LPS | Smooth | E. coli | 026B6 | Difco | +++++ | +++++ | +++++ | + |
| LPS | Smooth | E. coli | 055B5 | Difco | +++ | ++++ | − | − |
| LPS | Smooth | E. coli | 075 | Univ. Edinburgh | +++ | +++++ | +++ | − |
| LPS | Smooth | E. coli | 086 | Univ. Edinburgh | +++++ | +++++ | ++++ | + |
| LPS | Smooth | E. coli | 0111B4 | Difco | +++++ | +++++ | +++++ | ++ |
| LPS | Smooth | E. coli | 0127B8 | Difco | +++++ | +++++ | +++++ | +++ |
| LPS | Smooth | E. coli | 0128B12 | Difco | − | − | − | − |
| LPS | Smooth | E. coli | K235 | List | ++++ | +++++ | +++ | − |
| LPS | Smooth | S. minnesota | wt | List | ++++ | ++++ | ++ | − |
| LPS | Smooth | S. typhimurium | wt | Difco | +++++ | +++++ | +++++ | + |
| LPS | cCore | E. coli | K12 | Univ. Edinburgh | +++++ | +++++ | +++++ | +++ |
| LPS | cCore | E. coli | C62 | Univ. Edinburgh | ++++++ | +++++ | +++++ | ++ |
| LPS | cCore | E. coli | R1 | Institut Borstel | ++++++ | +++++ | +++++ | +++ |
| LPS | cCore | E. coli | R2 | Institut Borstel | +++++ | +++++ | +++++ | ++++ |
| LPS | cCore | E. coli | R3 | Institut Borstel | +++++ | +++++ | +++++ | ++ |
| LPS | cCore | E. coli | R4 | Institut Borstel | ++++++ | +++++ | +++++ | ++++ |
| LPS | cCore | S. minnesota | Ra R60 | List | ++++++ | +++++ | +++++ | ++++ |
| LPS | cCore | S. typhimurium | TV119 | Sigma | ++++++ | +++++ | +++++ | + |
| LPS | cCore | S. typhimurium | 1542 | Univ. Edinburgh | +++++ | +++++ | +++++ | ++ |
| LPS | cCore | K. aerogenes | M10B | Univ. Edinburgh | − | − | − | − |
| LPS | Rb2 | S. minnesota | R345 | List | ++++++ | +++++ | ++ | − |
| LPS | Rc | E. coli | J5 | List | ++++++ | +++++ | +++++ | ++++ |
| LPS | Rc | S. typhimurium | 878 | Univ. Edinburgh | ++++++ | ++++++ | +++++ | ++++ |
| LPS | Rc | P. typhimurium | SL684 | Sigma | +++++ | +++++ | +++++ | ++++ |
| LPS | Rc | P. aeruginosa | PAC605 | Univ. Edinburgh | − | − | − | − |
| LPS | RcP⁻ | S. minnesota | R5 | List | ++++++ | +++++ | +++++ | +++ |
| LPS | Rd2 | E. coli | F583 | Sigma | +++ | ++ | − | − |
| LPS | Rd1P⁻ | S. minnesota | R7 | List | − | − | − | − |
| LPS | Rd2 | S. minnesota | R4 | Institut Borstel | − | − | − | − |
| LPS | Re | E. coli | K12 (D31m4) | List | − | − | − | − |
| LPS | Re | E. coli | F515 | Institut Borstel | − | − | − | − |
| LPS | Re | S. minnesota | R595 | List | − | − | − | − |
| LPS | Re | S. typhimurium | SL1102 | Univ. Edinburgh | − | − | − | − |
| LPS | Re | S. typhimurium | SL1181 | Sigma | − | − | − | − |
| Lipid A | | E. coli | K12 (ex-D31m4) | List | − | − | − | − |
| Lipid A | | S. minnesota | R595 | List | + | ++ | − | − |
| BSA | | | | | − | − | − | − |

Purified native LPS (2 μg/ml) were used to coat the plates
Values are reported as O.D., one + equals 0.5 O.D. (405 nm).
BSA = bovine serum albumin

TABLE IID

| CHEMOTYPE | | STRAIN | | SUPPLIER | 1 μg/ml | SZ 27 19.16.7 100 ng/ml | 10 ng/ml | 1 ng/ml |
|---|---|---|---|---|---|---|---|---|
| LPS | Smooth | *E. coli* | 02 | Univ. Edinburgh | ++ | + | − | − |
| LPS | Smooth | *E. coli* | 06 | Univ. Edinburgh | − | − | − | − |
| LPS | Smooth | *E. coli* | 012 | Univ. Edinburgh | +++++ | ++++++ | ++++ | + |
| LPS | Smooth | *E. coli* | 015 | Univ. Edinburgh | + | +++ | ++ | − |
| LPS | Smooth | *E. coli* | 016 | Univ. Edinburgh | − | − | − | − |
| LPS | Smooth | *E. coli* | 018K− | Univ. Edinburgh | + | +++ | − | − |
| LPS | Smooth | *E. coli* | 018K+ | Univ. Edinburgh | ++++ | ++++ | ++ | − |
| LPS | Smooth | *E. coli* | 026B6 | Difco | +++++ | +++++ | +++ | − |
| LPS | Smooth | *E. coli* | 055B5 | Difco | − | − | − | − |
| LPS | Smooth | *E. coli* | 075 | Univ. Edinburgh | + | + | − | − |
| LPS | Smooth | *E. coli* | 086 | Univ. Edinburgh | ++ | ++++ | +++ | − |
| LPS | Smooth | *E. coli* | 0111B4 | Difco | +++++ | +++++ | +++++ | + |
| LPS | Smooth | *E. coli* | 0127B8 | Difco | ++++++ | +++++ | +++++ | + |
| LPS | Smooth | *E. coli* | 0128B12 | Difco | − | − | − | − |
| LPS | Smooth | *E. coli* | K235 | List | +++ | ++ | ++ | − |
| LPS | Smooth | *S. minnesota* | wt | List | ++ | − | − | − |
| LPS | Smooth | *S. typhimurium* | wt | Difco | +++++ | +++++ | +++ | − |
| LPS | cCore | *E. coli* | K12 | Univ. Edinburgh | +++++ | +++++ | +++++ | + |
| LPS | cCore | *E. coli* | C62 | Univ. Edinburgh | +++++ | +++++ | +++++ | + |
| LPS | cCore | *E. coli* | R1 | Institut Borstel | +++++ | +++++ | +++++ | + |
| LPS | cCore | *E. coli* | R2 | Institut Borstel | ++++++ | +++++ | +++++ | + |
| LPS | cCore | *E. coli* | R3 | Institut Borstel | +++++ | +++++ | +++++ | + |
| LPS | cCore | *E. coli* | R4 | Institut Borstel | +++++ | +++++ | +++++ | + |
| LPS | cCore | *S. minnesota* | Ra R60 | List | +++++ | +++++ | +++++ | + |
| LPS | cCore | *S. typhimurium* | TV119 | Sigma | +++++ | +++++ | ++ | − |
| LPS | cCore | *S. typhimurium* | 1542 | Univ. Edinburgh | +++++ | +++++ | ++++ | + |
| LPS | cCore | *K. aerogenes* | M10B | Univ. Edinburgh | − | − | − | − |
| LPS | Rb2 | *S. minnesota* | R345 | List | +++++ | ++++ | ++ | − |
| LPS | Rc | *E. coli* | J5 | List | +++++ | +++++ | +++++ | + |
| LPS | Rc | *S. typhimurium* | 878 | Univ. Edinburgh | +++++ | +++++ | +++++ | + |
| LPS | Rc | *P. typhimurium* | SL684 | Sigma | ++++++ | +++++ | +++++ | + |
| LPS | Rc | *P. aeruginosa* | PAC605 | Univ. Edinburgh | + | − | − | − |
| LPS | RcP− | *S. minnesota* | R5 | List | +++++ | +++++ | ++++ | + |
| LPS | Rd2 | *E. coli* | F583 | Sigma | − | − | − | − |
| LPS | Rd1P− | *S. minnesota* | R7 | List | − | − | − | − |
| LPS | Rd2 | *S. minnesota* | R4 | Institut Borstel | − | − | + | + |
| LPS | Re | *E. coli* | K12 (D31m4) | List | − | − | − | − |
| LPS | Re | *E. coli* | F515 | Institut Borstel | − | − | − | − |
| LPS | Re | *S. minnesota* | R595 | List | − | − | − | − |
| LPS | Re | *S. typhimurium* | SL1102 | Univ. Edinburgh | − | − | − | − |
| LPS | Re | *S. typhimurium* | SL1181 | Sigma | − | − | − | − |
| Lipid A | | *E. coli* | K12 (ex-D31m4) | List | − | − | − | − |
| Lipid A | | *S. minnesota* | R595 | List | − | − | − | − |
| BSA | | | | | − | − | − | − |

Purified native LPS (2 μg/ml) were used to coat the plates
Values are reported as O.D., one + equals 0.5 O.D. (405 nm).
BSA = bovine serum albumin

TABLE IIIA

| CHEMOTYPE | | STRAIN | | SUPPLIER | WNl 222–5 100 ng/nl |
|---|---|---|---|---|---|
| Bacteria | smooth | *E. coli* | 01 | Univ. Edinburgh | +++++ |
| Bacteria | smooth | *E. coli* | 04 | Univ. Edinburgh | +++++ |
| Bacteria | smooth | *E. coli* | 06 | Univ. Edinburgh | +++++ |
| Bacteria | smooth | *E. coli* | 015 | Univ. Edinburgh | +++++ |
| Bacteria | smooth | *E. coli* | 016 | Univ. Edinburgh | +++++ |
| Bacteria | smooth | *E. coli* | 018K− | Univ. Edinburgh | +++++ |
| Bacteria | smooth | *E. coli* | 075 | Univ. Edinburgh | |
| Bacteria | cCore | *E. coli* | K12 | Univ. Edinburgh | +++++ |
| Bacteria | cCore | *E. coli* | C62 | Univ. Edinburgh | +++++ |
| Bacteria | cCore | *E. coli* | R1 | Institut Borstel | +++++ |
| Bacteria | cCore | *E. coli* | R2 | Institut Borstel | +++++ |
| Bacteria | cCore | *E. coli* | R3 | Institut Borstel | +++++ |
| Bacteria | cCore | *E. coli* | R4 | Institut Borstel | +++++ |
| Bacteria | cCore | *S. minnesota* | Ra R60 | Univ. Edinburgh | +++++ |
| Bacteria | cCore | *S. typhimurium* | 1135 | Univ. Edinburgh | +++++ |
| Bacteria | cCore | *S. typhimurium* | 1542 | Univ. Edinburgh | +++++ |
| Bacteria | cCore | *K. aerogenes* | M10B | Univ. Edinburgh | − |
| Bacteria | Rb | *S. minnesota* | R345 | Univ. Edinburgh | +++++ |

TABLE IIIA-continued

| CHEMOTYPE | | STRAIN | SUPPLIER | WN1 222–5 100 ng/nl |
|---|---|---|---|---|
| Bacteria Rc | E. coli | J5 | Univ. Edinburgh | +++++ |
| Bacteria Rc | S. typhimurium | 878 | Univ. Edinburgh | +++++ |
| Bacteria Rc | P. aeruginosa | PAC 605 | Univ. Edinburgh | − |
| Bacteria Rc | S. minnesota | R5 | Univ. Edinburgh | +++++ |
| Bacteria Rd1P- | S. minnesota | R7 | Univ. Edinburgh | +++++ |
| Bacteria Rd2 | S. minnesota | R4 | Univ. Edinburgh | − |
| Bacteria Re | E. coli | F515 | Institut Borstel | − |
| Bacteria Re | S. minnesota | R595 | Univ. Edinburgh | − |
| Bacteria Re | S. typhimurium | SL1102 | Univ. Edinburgh | + |
| BSA | | | | − |

Heat killed bacteria (0.5 × $10^8$ cell/ml) were used to coat the plates
Values are reported as O.D., one + equals 0.5 O.D. (405 nm).

TABLE IIIB

| CHEMOTYPE | | STRAIN | SUPPLIER | WN1 58–9 100 ng/nl |
|---|---|---|---|---|
| Bacteria smooth | E. coli | 01 | Univ. Edinburgh | +++++ |
| Bacteria smooth | E. coli | 04 | Univ. Edinburgh | +++++ |
| Bacteria smooth | E. coli | 06 | Univ. Edinburgh | +++++ |
| Bacteria smooth | E. coli | 015 | Univ. Edinburgh | +++++ |
| Bacteria smooth | E. coli | 016 | Univ. Edinburgh | +++++ |
| Bacteria smooth | E. coli | 018K- | Univ. Edinburgh | +++++ |
| Bacteria smooth | E. coli | 075 | Univ. Edinburgh | |
| Bacteria cCore | E. coli | K12 | Univ. Edinburgh | +++++ |
| Bacteria cCore | E. coli | C62 | Univ. Edinburgh | +++++ |
| Bacteria cCore | E. coli | R1 | Institut Borstel | +++++ |
| Bacteria cCore | E. coli | R2 | Institut Borstel | +++++ |
| Bacteria cCore | E. coli | R3 | Institut Borstel | +++++ |
| Bacteria cCore | E. coli | R4 | Institut Borstel | ++++ |
| Bacteria cCore | S. minnesota | Ra R60 | Univ. Edinburgh | +++++ |
| Bacteria cCore | S. typhimurium | 1135 | Univ. Edinburgh | +++++ |
| Bacteria cCore | S. typhimurium | 1542 | Univ. Edinburgh | +++++ |
| Bacteria cCore | K. aerogenes | M10B | Univ. Edinburgh | − |
| Bacteria Rb | S. minnesota | R345 | Univ. Edinburgh | ++++ |
| Bacteria Rc | E. coli | J5 | Univ. Edinburgh | +++++ |
| Bacteria Rc | S. typhimurium | 878 | Univ. Edinburgh | +++++ |
| Bacteria Rc | P. aeruginosa | PAC 605 | Univ. Edinburgh | − |
| Bacteria Rc | S. minnesota | R5 | Univ. Edinburgh | +++++ |
| Bacteria Rd1P- | S. minnesota | R7 | Univ. Edinburgh | +++++ |
| Bacteria Rd2 | S. minnesota | R4 | Univ. Edinburgh | − |
| Bacteria Re | E. coli | F515 | Institut Borstel | − |
| Bacteria Re | S. minnesota | R595 | Univ. Edinburgh | − |
| Bacteria Re | S. typhimurium | SL1102 | Univ. Edinburgh | + |
| BSA | | | | − |

Heat killed bacteria (0.5 × $10^8$ cell/ml) were used to coat the plates
Values are reported as O.D., one + equals 0.5 O.D. (405 nm).

TABLE IIIC

| CHEMOTYPE | | STRAIN | SUPPLIER | H1 61–2 IgG1 | | | |
|---|---|---|---|---|---|---|---|
| | | | | 1 µg/ml | 100 ng/ml | 10 ng/ml | 1 ng/nl |
| Bacteria smooth | E. coli | 01 | Univ. Edinburgh | +++++ | +++++ | +++++ | +++ |
| Bacteria smooth | E. coli | 04 | Univ. Edinburgh | +++++ | +++++ | +++++ | ++ |
| Bacteria smooth | E. coli | 06 | Univ. Edinburgh | +++++ | +++++ | +++++ | ++ |
| Bacteria smooth | E. coli | 015 | Univ. Edinburgh | +++++ | +++++ | +++++ | + |
| Bacteria smooth | E. coli | 016 | Univ. Edinburgh | +++++ | +++++ | +++++ | +++ |
| Bacteria smooth | E. coli | 018K- | Univ. Edinburgh | + | − | − | − |
| Bacteria smooth | E. coli | 075 | Univ. Edinburgh | +++++ | +++++ | +++++ | ++++ |
| Bacteria cCore | E. coli | K12 | Univ. Edinburgh | +++++ | +++++ | +++++ | +++ |
| Bacteria cCore | E. coli | C62 | Univ. Edinburgh | +++++ | +++++ | +++++ | ++++ |
| Bacteria cCore | E. coli | R1 | Institut Borstel | +++++ | +++++ | +++++ | +++ |
| Bacteria cCore | E. coli | R2 | Institut Borstel | +++++ | +++++ | +++++ | ++++ |
| Bacteria cCore | E. coli | R3 | Institut Borstel | +++++ | +++++ | +++++ | ++++ |
| Bacteria cCore | E. coli | R4 | Institut Borstel | +++++ | +++++ | +++++ | ++++ |
| Bacteria cCore | S. minnesota | Ra R60 | Univ. Edinburgh | ++++++ | +++++ | +++++ | +++ |

TABLE IIIC-continued

| | | | | H1 61–2 IgGl | | | |
|---|---|---|---|---|---|---|---|
| CHEMOTYPE | STRAIN | | SUPPLIER | 1 μg/ml | 100 ng/ml | 10 ng/ml | 1 ng/nl |
| Bacteria cCore | S. typhimurium | 1135 | Univ. Edinburgh | +++++ | +++++ | +++++ | ++++ |
| Bacteria cCore | S. typhimurium | 1542 | Univ. Edinburgh | +++++ | +++++ | +++++ | ++++ |
| Bacteria cCore | K. aerogenes | M10B | Univ. Edinburgh | – | – | – | – |
| Bacteria Rb | S. minnesota | R345 | Univ. Edinburgh | ++ | + | – | – |
| Bacteria Rc | E. coli | J5 | Univ. Edinburgh | +++++ | +++++ | +++++ | ++ |
| Bacteria Rc | S. typhimurium | 878 | Univ. Edinburgh | +++++ | +++++ | +++++ | +++ |
| Bacteria Rc | P. aeruginosa | PAC 605 | Univ. Edinburgh | – | – | – | – |
| Bacteria Rc | S. minnesota | R5 | Univ. Edinburgh | +++++ | +++++ | +++++ | ++ |
| Bacteria Rd1P- | S. minnesota | R7 | Univ. Edinburgh | +++++ | ++++ | ++ | + |
| Bacteria Rd2 | S. minnesota | R4 | Univ. Edinburgh | – | – | – | – |
| Bacteria Re | E. coli | F515 | Institut Borstel | – | – | – | |
| Bacteria Re | S. minnesota | R595 | Univ. Edinburgh | – | – | – | – |
| Bacteria Re | S. typhimurium | SL1102 | Univ. Edinburgh | – | – | – | – |
| BSA | | | | – | – | – | – |

Heat killed bacteria (0.5 × 10$^8$ cell/ml) were used to coat the plates
Values are reported as O.D., one + equals 0.5 O.D. (405 nm).

TABLE IIID

| | | | | SZ 27 19.16.7 | | | |
|---|---|---|---|---|---|---|---|
| CHEMOTYPE | STRAIN | | SUPPLIER | 1 μg/ml | 100 ng/ml | 10 ng/ml | 1 ng/nl |
| Bacteria smooth | E. coli | 01 | Univ. Edinburgh | ++++++ | +++++ | +++++ | ++ |
| Bacteria smooth | E. coli | 04 | Univ. Edinburgh | ++++++ | +++++ | +++++ | ++ |
| Bacteria smooth | E. coli | 06 | Univ. Edinburgh | +++++ | +++++ | +++++ | ++ |
| Bacteria smooth | E. coli | 015 | Univ. Edinburgh | ++++++ | +++++ | +++++ | + |
| Bacteria smooth | E. coli | 016 | Univ. Edinburgh | ++++++ | +++++ | +++++ | ++ |
| Bacteria smooth | E. coli | 018K- | Univ. Edinburgh | ++++ | +++ | + | – |
| Bacteria smooth | E. coli | 075 | Univ. Edinburgh | +++++ | ++++ | +++++ | + |
| Bacteria cCore | E. coli | K12 | Univ. Edinburgh | +++++ | +++++ | +++++ | ++ |
| Bacteria cCore | E. coli | C62 | Univ. Edinburgh | +++++ | +++++ | +++++ | ++ |
| Bacteria cCore | E. coli | R1 | Institut Borstel | +++++ | +++++ | +++++ | + |
| Bacteria cCore | E. coli | R2 | Institut Borstel | +++++ | +++++ | +++++ | + |
| Bacteria cCore | E. coli | R3 | Institut Borstel | +++++ | +++++ | +++++ | + |
| Bacteria cCore | E. coli | R4 | Institut Borstel | +++++ | +++++ | +++++ | ++ |
| Bacteria cCore | S. minnesota | Ra R60 | Univ. Edinburgh | +++++ | +++++ | +++++ | + |
| Bacteria cCore | S. typhimurium | 1135 | Univ. Edinburgh | ++++++ | +++++ | +++++ | + |
| Bacteria cCore | S. typhimurium | 1542 | Univ. Edinburgh | ++++++ | +++++ | +++++ | ++ |
| Bacteria cCore | K. aerogenes | M10B | Univ. Edinburgh | – | – | – | – |
| Bacteria Rb | S. minnesota | R345 | Univ. Edinburgh | + | – | – | – |
| Bacteria Rc | E. coli | J5 | Univ. Edinburgh | ++++++ | +++++ | +++++ | + |
| Bacteria Rc | S. typhimurium | 878 | Univ. Edinburgh | ++++++ | +++++ | +++++ | + |
| Bacieria Rc | P. aeruginosa | PAC 605 | Univ. Edinburgh | – | – | – | – |
| Bacteria Rc | S. minnesota | R5 | Univ. Edinburgh | ++++++ | +++++ | +++++ | + |
| Bacteria Rd1P- | S. minnesota | R7 | Univ. Edinburgh | +++++ | ++++ | ++ | – |
| Bacteria Rd2 | S. minnesota | R4 | Univ. Edinburgh | – | – | – | – |
| Bacteria Re | E. coli | F515 | Institut Borstel | – | – | – | – |
| Bacteria Re | S. minnesota | R595 | Univ. Edinburgh | – | – | – | – |
| Bacteria Re | S. typhimurium | SL1102 | Univ. Edinburgh | – | – | – | – |
| BSA | | | | – | – | – | – |

Heat killed bacteria (0.5 × 10$^8$ cell/ml) were used to coat the plates
Values are reported as O.D., one + equals 0.5 O.D. (405 nm).

We claim:

1. A monoclonal antibody which binds an epitope in the core region of the LPS molecule and which is cross-reactive to, and cross-protective against endotoxemia caused by, at least two different Gram-negative bacterial strains having different core structures, said bacterial strains selected from the group consisting of:
   (a) smooth *E. coli*,
   (b) rough mutant *E. coli* of core types R1, R2, R3, R4 and K12; and
   (c) Salmonella;
said monoclonal antibody having a constant region of human origin, a variable framework region of human or non-human origin, and a hypervariable region of non-human origin.

2. A monoclonal antibody according to claim 1 which binds an epitope which is completely present in the Rc core structure of *E. coli* and is also present in the complete core.

3. A monoclonal antibody according to claim 1 wherein the hypervariable region is of murine origin.

4. A monoclonal antibody according to any one of the preceding claims which is of IgG isotype.

5. A hybridoma cell line producing a monoclonal antibody according to any one of the preceding claims.

6. A method for the production of a monoclonal antibody according to claim 1 characterized by the steps of
   a) Immunizing an animal with a plurality of types of LPS molecule
   b) Fusing spleen cells from the animal with an immortalizing cell line to produce hybridomas
   c) Screening the hybridomas to select those producing cross-reactive antibodies
   d) Further screening the hybridomas to select those producing protective antibodies
   and e) Growing the selected hybridoma and isolating the antibody produced.

7. A method according to claim 6 in which the animal is immunized with a cocktail of different rough strains of heat-killed Gram-negative bacteria.

8. A method according to claim 6 in which the animal is immunized sequentially with a number of different rough strains of heat-killed Gram- negative bacteria, only one strain being administered at any one time.

9. A method according to one of claim 6 which comprises the additional step between steps a) and b):
   a') Carrying out an initial screening on the serum of the immunized animal to test the strength and plurality of its immune response, selecting animals with a strong response, and giving such animals a booster immunization before removing its spleen cells.

10. A method according to claim 6 in which the screening step c) is carried out in an ELISA assay using a series of mixtures of different smooth and rough LPS types.

11. An LPS binding molecule which comprises at least one antigen binding site comprising at least one domain which comprises in sequence framework region hFR1, hypervariable region hCDR1, framework region hFR2, hypervariable region hCDR2, framework region hFR3, hypervariable region hCDR3, and framework region hFR4;
    said hCDR1 having the amino acid sequence Asp Tyr Tyr Met Thr which are amino acids 31–35 of SEQ ID NO:2 or SEQ ID NO:4;
    said hCDR2 having the amino acid sequence 50–67 of SEQ ID NO:2
       wherein amino acid 54 is Lys or Tyr and amino acid 67 is Lys or Arg;
    said hCDR3 having the amino acid sequence Gln Gly Arg Gly Tyr Thr Leu Asp Tyr which are amino acids 101–109 of SEQ ID NO:2 or SEO ID NO:4;
       and direct equivalents thereof, said LPS binding molecule which binds an epitope in the core region of the LPS molecule of gram negative bacterial strains having different core structures and selected from the group consisting of smooth *E. coli*; rough *E. coli* of core types R1, R2, R3, R4 and K12; and Salmonella.

12. A single domain antibody according to claim 11 comprising in sequence the hypervariable regions hCDR1, hCDR2 and hCDR3 associated with murine or human heavy chain framework regions so as to form an isolated heavy chain variable domain.

13. An LPS binding molecule according to claim 11 comprising at least one antigen binding site comprising:
   a) a first domain comprising the hypervariable regions hCDR1, hCDR2 and hCDR3 as defined in claim 11 and,
   b) a second domain comprising in sequence framework region lFR1, hypervariable region lCDR1, framework region lFR2, hypervariable region lCDR2, framework region lFR3, hypervariable region lCDR3, and framework region lFR4;
      said lCDR1 having the amino acid sequence 24–34 of SEQ ID NO:6
   wherein amino acid 26 is Ser or Arg and amino acid 27 is Gln or Leu; said lCDR2 having the amino acid sequence Lys Ala Ser Asn Leu His Thr which are amino acids 50–56 of SEQ ID NO:6 or SEQ ID NO:8;
      said lCDR3 having the amino acid sequence Leu Gln Gly Gln Ser Tyr Pro Arg Thr which are amino acids 89–97 of SEQ ID NO:6 or SEQ ID NO:8;
   and direct equivalents thereof.

14. An LPS binding molecule according to claim 13 in which the hypervariable regions are associated with murine or human framework regions.

15. An LPS binding molecule according to claim 13 in which the first and the second domains are part of a single common peptide chain.

16. An LPS binding molecule according to claim 15 in which the first and the second domains are respectively an Ig heavy chain variable domain and an Ig light chain variable domain, and are covalently bound by a peptide linker consisting of from 10 to 30 amino acids.

17. An LPS binding molecule according to claim 13 in which the first domain is part of a heavy chain of at least a fragment of an Ig molecule, and the second domain is part of a light chain of at least a fragment of an Ig molecule.

18. An LPS binding molecule according to claim 17 which is a complete Ig molecule.

19. An Ig molecule according to claim 18 which is of IgG isotype.

20. An Ig molecule according to claim 18 which is murine.

21. An Ig molecule according to claim 18 in which the variable domains are murine and the constant domains are human.

22. An Ig molecule according to claim 18 in which the framework regions and the constant domains are human.

23. An Ig molecule according to claim 20 in which the amino acid sequence of the heavy chain variable domain is a direct equivalent of SEQ ID NO:2 or alternatively a direct sequence of SEQ ID NO:4 and the amino acid sequence of the light chain variable domain is a direct equivalent of SEQ ID NO:6 or alternatively a direct equivalent of SEQ ID NO:8.

24. An Ig molecule according to claim 23, in which the heavy chain constant domain is of human type $\gamma_1$ and the light chain constant domain is of human type $\kappa$.

25. An LPS binding molecule according to any one of claims 11–24 for use as a pharmaceutical agent.

26. A pharmaceutical composition comprising an LPS binding molecule according to any one of claims 11–24 in association with a pharmaceutically acceptable diluent or carrier.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 361 base pairs
        ( B ) TYPE: nucleic acid
        ( C ) STRANDEDNESS: double
        ( D ) TOPOLOGY: linear (ii) MOLECULE TYPE: cDNA to mRNA (iii) HYPOTHETICAL: NO (ix) FEATURE:
        (A) NAME/KEY: CDS
        (B) LOCATION: 1..361

(xi) SEQUENCE DESCRIPTION: SEQ ID NO: 1:

| GAG | GTG | AAG | CTG | GTG | GAG | TCT | GGA | GGA | GGC | TTG | GTA | CAG | CCG | GGG | GGT | 48 |
| Glu | Val | Lys | Leu | Val | Glu | Ser | Gly | Gly | Gly | Leu | Val | Gln | Pro | Gly | Gly | |
| 1 | | | | 5 | | | | | 10 | | | | | 15 | | |

| TCT | CTG | AGT | CTC | TCC | TGT | GCA | GCT | TCT | GGA | TTC | ACC | TTC | AGT | GAT | TAC | 96 |
| Ser | Leu | Ser | Leu | Ser | Cys | Ala | Ala | Ser | Gly | Phe | Thr | Phe | Ser | Asp | Tyr | |
| | | | | 20 | | | | 25 | | | | | 30 | | | |

| TAC | ATG | ACC | TGG | GTC | CGC | CAG | GCT | CCA | GGG | AAG | GCA | CCT | GAG | TGG | TTG | 144 |
| Tyr | Met | Thr | Trp | Val | Arg | Gln | Ala | Pro | Gly | Lys | Ala | Pro | Glu | Trp | Leu | |
| | | 35 | | | | 40 | | | | | 45 | | | | | |

| GCT | TTG | ATT | AGA | AAC | AAA | CGT | AAT | GGT | GAC | ACA | GCA | GAG | TAT | AGT | GCA | 192 |
| Ala | Leu | Ile | Arg | Asn | Lys | Arg | Asn | Gly | Asp | Thr | Ala | Glu | Tyr | Ser | Ala | |
| | 50 | | | | 55 | | | | | 60 | | | | | | |

| TCT | GTG | AAG | GGT | CGG | TTC | ACC | ATC | TCC | AGA | GAT | TAT | TCC | CGA | AGC | ATC | 240 |
| Ser | Val | Lys | Gly | Arg | Phe | Thr | Ile | Ser | Arg | Asp | Tyr | Ser | Arg | Ser | Ile | |
| 65 | | | | | 70 | | | | | 75 | | | | | 80 | |

| CTC | CAT | CTT | CAA | ATG | AAT | GCC | CTG | AGA | ACT | GAG | GAC | AGT | GCC | ACT | TAT | 288 |
| Leu | His | Leu | Gln | Met | Asn | Ala | Leu | Arg | Thr | Glu | Asp | Ser | Ala | Thr | Tyr | |
| | | | | 85 | | | | | 90 | | | | | 95 | | |

| TAT | TGT | GTA | AGA | CAG | GGA | CGG | GGC | TAT | ACT | TTG | GAC | TAT | TGG | GGT | CAA | 336 |
| Tyr | Cys | Val | Arg | Gln | Gly | Arg | Gly | Tyr | Thr | Leu | Asp | Tyr | Trp | Gly | Gln | |
| | | | 100 | | | | | 105 | | | | | 110 | | | |

| GGA | ACC | TCA | GTC | ACC | GTC | TCC | TCA | G | | | | | | | | 361 |
| Gly | Thr | Ser | Val | Thr | Val | Ser | Ser | | | | | | | | | |
| | | 115 | | | | | 120 | | | | | | | | | |

(2) INFORMATION FOR SEQ ID NO: 2:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 2:

| Glu | Val | Lys | Leu | Val | Glu | Ser | Gly | Gly | Gly | Leu | Val | Gln | Pro | Gly | Gly |
| 1 | | | | 5 | | | | | 10 | | | | | 15 | |

| Ser | Leu | Ser | Leu | Ser | Cys | Ala | Ala | Ser | Gly | Phe | Thr | Phe | Ser | Asp | Tyr |
| | | | | 20 | | | | 25 | | | | | 30 | | |

| Tyr | Met | Thr | Trp | Val | Arg | Gln | Ala | Pro | Gly | Lys | Ala | Pro | Glu | Trp | Leu |
| | | 35 | | | | 40 | | | | | 45 | | | | |

| Ala | Leu | Ile | Arg | Asn | Lys | Arg | Asn | Gly | Asp | Thr | Ala | Glu | Tyr | Ser | Ala |
| | 50 | | | | 55 | | | | | 60 | | | | | |

| Ser | Val | Lys | Gly | Arg | Phe | Thr | Ile | Ser | Arg | Asp | Tyr | Ser | Arg | Ser | Ile |
| 65 | | | | | 70 | | | | | 75 | | | | | 80 |

| Leu | His | Leu | Gln | Met | Asn | Ala | Leu | Arg | Thr | Glu | Asp | Ser | Ala | Thr | Tyr |
| | | | | 85 | | | | | 90 | | | | | 95 | |

| Tyr | Cys | Val | Arg | Gln | Gly | Arg | Gly | Tyr | Thr | Leu | Asp | Tyr | Trp | Gly | Gln |
| | | | 100 | | | | | 105 | | | | | 110 | | |

| Gly | Thr | Ser | Val | Thr | Val | Ser | Ser |
| | | 115 | | | | | 120 |

( 2 ) INFORMATION FOR SEQ ID NO: 3:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i x ) FEATURE:
        ( A ) NAME/KEY: CDS
        ( B ) LOCATION: 1..360

( x i ) SEQUENCE DESCRIPTION: SEQ ID NO: 3:

```
GAG  GTG  AAG  CTG  GTG  GAG  TCT  GGA  GGA  GGC  TTG  GTA  CAG  CCT  GGG  GGT         48
Glu  Val  Lys  Leu  Val  Glu  Ser  Gly  Gly  Gly  Leu  Val  Gln  Pro  Gly  Gly
 1              5                        10                       15

TCT  CTG  CGT  CTC  TCC  TGT  GCA  GCT  TCT  GGA  TTC  ACC  TTC  ATT  GAT  TAC         96
Ser  Leu  Arg  Leu  Ser  Cys  Ala  Ala  Ser  Gly  Phe  Thr  Phe  Ile  Asp  Tyr
           20                        25                       30

TAC  ATG  ACC  TGG  GTC  CGC  CAT  CCG  CCA  GGG  GAG  GCA  CCT  GAA  TGG  TTG        144
Tyr  Met  Thr  Trp  Val  Arg  His  Pro  Pro  Gly  Glu  Ala  Pro  Glu  Trp  Leu
      35                        40                       45

GCT  TTG  ATT  AGA  AAC  TAC  CGT  AAT  GGT  GAC  ACA  GCA  GAA  TAC  AGT  GCA        192
Ala  Leu  Ile  Arg  Asn  Tyr  Arg  Asn  Gly  Asp  Thr  Ala  Glu  Tyr  Ser  Ala
      50                        55                       60

TCT  GTG  AGG  GGT  CGG  TTC  ACC  ATC  TCC  AGA  GAT  GAT  TCC  CAA  AGC  ATC        240
Ser  Val  Arg  Gly  Arg  Phe  Thr  Ile  Ser  Arg  Asp  Asp  Ser  Gln  Ser  Ile
 65                       70                       75                       80

CTC  TAT  CTT  CAA  ATG  AAT  GCC  CTG  AGA  GCT  GAG  GAC  AGT  GCC  ACT  TAT        288
Leu  Tyr  Leu  Gln  Met  Asn  Ala  Leu  Arg  Ala  Glu  Asp  Ser  Ala  Thr  Tyr
                     85                        90                       95

TAC  TGT  GTA  AGA  CAG  GGA  CGG  GGC  TAT  ACT  CTG  GAC  TAC  TGG  GGT  CAA        336
Tyr  Cys  Val  Arg  Gln  Gly  Arg  Gly  Tyr  Thr  Leu  Asp  Tyr  Trp  Gly  Gln
           100                       105                      110

GGA  ACC  TCA  GTC  ACC  GTC  TCC  TCA                                                 360
Gly  Thr  Ser  Val  Thr  Val  Ser  Ser
           115                      120
```

( 2 ) INFORMATION FOR SEQ ID NO: 4:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Glu  Val  Lys  Leu  Val  Glu  Ser  Gly  Gly  Gly  Leu  Val  Gln  Pro  Gly  Gly
 1              5                        10                       15

Ser  Leu  Arg  Leu  Ser  Cys  Ala  Ala  Ser  Gly  Phe  Thr  Phe  Ile  Asp  Tyr
           20                        25                       30

Tyr  Met  Thr  Trp  Val  Arg  His  Pro  Pro  Gly  Glu  Ala  Pro  Glu  Trp  Leu
      35                        40                       45

Ala  Leu  Ile  Arg  Asn  Tyr  Arg  Asn  Gly  Asp  Thr  Ala  Glu  Tyr  Ser  Ala
      50                        55                       60

Ser  Val  Arg  Gly  Arg  Phe  Thr  Ile  Ser  Arg  Asp  Asp  Ser  Gln  Ser  Ile
 65                       70                       75                       80

Leu  Tyr  Leu  Gln  Met  Asn  Ala  Leu  Arg  Ala  Glu  Asp  Ser  Ala  Thr  Tyr
                     85                        90                       95
```

| Tyr | Cys | Val | Arg | Gln | Gly | Arg | Gly | Tyr | Thr | Leu | Asp | Tyr | Trp | Gly | Gln |
|     |     |     | 100 |     |     |     |     | 105 |     |     |     |     | 110 |     |     |

| Gly | Thr | Ser | Val | Thr | Val | Ser | Ser |
|     |     | 115 |     |     |     |     | 120 |

(2) INFORMATION FOR SEQ ID NO: 5:

(i) SEQUENCE CHARACTERISTICS:
        (A) LENGTH: 322 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (ix) FEATURE:
        (A) NAME/KEY: CDS
        (B) LOCATION: 1..322

(xi) SEQUENCE DESCRIPTION: SEQ ID NO: 5:

| GAC | ATC | CAG | ATG | AAC | CAG | TCT | CCA | TCC | AGT | CTG | TCT | GCA | TCC | CTC | GGA | 48 |
| Asp | Ile | Gln | Met | Asn | Gln | Ser | Pro | Ser | Ser | Leu | Ser | Ala | Ser | Leu | Gly |    |
| 1   |     |     |     | 5   |     |     |     |     | 10  |     |     |     |     | 15  |     |    |

| GAC | ACA | ATT | TCC | ATC | ACT | TGC | CGT | GCC | AGT | CAG | AAC | ATT | AAT | ATT | TGG | 96 |
| Asp | Thr | Ile | Ser | Ile | Thr | Cys | Arg | Ala | Ser | Gln | Asn | Ile | Asn | Ile | Trp |    |
|     |     |     | 20  |     |     |     |     | 25  |     |     |     |     | 30  |     |     |    |

| TTA | AGC | TGG | TAT | CAG | CAA | AAA | CCA | GGA | AAT | GTT | CCT | AAA | CTT | TTA | ATC | 144 |
| Leu | Ser | Trp | Tyr | Gln | Gln | Lys | Pro | Gly | Asn | Val | Pro | Lys | Leu | Leu | Ile |     |
|     |     |     | 35  |     |     |     |     | 40  |     |     |     |     | 45  |     |     |     |

| TAT | AAG | GCT | TCC | AAC | TTG | CAC | ACA | GGC | GTC | CCA | TCA | AGG | TTT | AGT | GGC | 192 |
| Tyr | Lys | Ala | Ser | Asn | Leu | His | Thr | Gly | Val | Pro | Ser | Arg | Phe | Ser | Gly |     |
|     | 50  |     |     |     |     | 55  |     |     |     |     | 60  |     |     |     |     |     |

| AGT | GGA | TCT | GGA | ACA | GAT | TTC | ACA | TTA | ATC | ATC | AGC | AGT | CTG | CAG | CCT | 240 |
| Ser | Gly | Ser | Gly | Thr | Asp | Phe | Thr | Leu | Ile | Ile | Ser | Ser | Leu | Gln | Pro |     |
| 65  |     |     |     |     | 70  |     |     |     |     | 75  |     |     |     |     | 80  |     |

| GAA | GAC | ATT | GCC | ACT | TAC | TAC | TGT | CTA | CAG | GGT | CAA | AGT | TAT | CCT | CGT | 288 |
| Glu | Asp | Ile | Ala | Thr | Tyr | Tyr | Cys | Leu | Gln | Gly | Gln | Ser | Tyr | Pro | Arg |     |
|     |     |     |     | 85  |     |     |     |     | 90  |     |     |     |     | 95  |     |     |

| ACG | TTC | GGT | GGA | GGC | ACC | AAG | CTG | GAG | ATC | AAA | C   | 322 |
| Thr | Phe | Gly | Gly | Gly | Thr | Lys | Leu | Glu | Ile | Lys |     |     |
|     |     |     | 100 |     |     |     |     | 105 |     |     |     |     |

(2) INFORMATION FOR SEQ ID NO: 6:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 6:

| Asp | Ile | Gln | Met | Asn | Gln | Ser | Pro | Ser | Ser | Leu | Ser | Ala | Ser | Leu | Gly |
| 1   |     |     |     | 5   |     |     |     |     | 10  |     |     |     |     | 15  |     |

| Asp | Thr | Ile | Ser | Ile | Thr | Cys | Arg | Ala | Ser | Gln | Asn | Ile | Asn | Ile | Trp |
|     |     |     | 20  |     |     |     |     | 25  |     |     |     |     | 30  |     |     |

| Leu | Ser | Trp | Tyr | Gln | Gln | Lys | Pro | Gly | Asn | Val | Pro | Lys | Leu | Leu | Ile |
|     |     |     | 35  |     |     |     |     | 40  |     |     |     |     | 45  |     |     |

| Tyr | Lys | Ala | Ser | Asn | Leu | His | Thr | Gly | Val | Pro | Ser | Arg | Phe | Ser | Gly |
|     | 50  |     |     |     |     | 55  |     |     |     |     | 60  |     |     |     |     |

| Ser | Gly | Ser | Gly | Thr | Asp | Phe | Thr | Leu | Ile | Ile | Ser | Ser | Leu | Gln | Pro |
| 65  |     |     |     |     | 70  |     |     |     |     | 75  |     |     |     |     | 80  |

Glu  Asp  Ile  Ala  Thr  Tyr  Tyr  Cys  Leu  Gln  Gly  Gln  Ser  Tyr  Pro  Arg
               85                           90                           95

Thr  Phe  Gly  Gly  Gly  Thr  Lys  Leu  Glu  Ile  Lys
               100                      105

( 2 ) INFORMATION FOR SEQ ID NO: 7:

( i ) SEQUENCE CHARACTERISTICS:
        ( A ) LENGTH: 321 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i x ) FEATURE:
        ( A ) NAME/KEY: CDS
        ( B ) LOCATION: 1..321

( x i ) SEQUENCE DESCRIPTION: SEQ ID NO: 7:

```
GAC  ATC  CAG  ATG  AAC  CAG  TCT  CCA  TCC  AGT  CTG  TCT  GCA  TCC  CTC  GGA        48
Asp  Ile  Gln  Met  Asn  Gln  Ser  Pro  Ser  Ser  Leu  Ser  Ala  Ser  Leu  Gly
 1                   5                        10                       15

GAC  ACA  ATT  ACC  ATC  ACT  TGC  CGT  GCC  AGA  CTG  AAC  ATT  AAT  ATT  TGG        96
Asp  Thr  Ile  Thr  Ile  Thr  Cys  Arg  Ala  Arg  Leu  Asn  Ile  Asn  Ile  Trp
                 20                       25                      30

TTA  AGT  TGG  TAC  CAG  CAG  AAA  GCA  GGA  AAT  ATT  CCT  AAA  CTT  TTG  ATC       144
Leu  Ser  Trp  Tyr  Gln  Gln  Lys  Ala  Gly  Asn  Ile  Pro  Lys  Leu  Leu  Ile
            35                       40                       45

TCT  AAG  GCT  TCC  AAC  TTG  CAC  ACA  GGC  GTC  CCA  TCA  AGG  TTT  AGT  GGC       192
Ser  Lys  Ala  Ser  Asn  Leu  His  Thr  Gly  Val  Pro  Ser  Arg  Phe  Ser  Gly
       50                       55                       60

AGT  GGA  TCT  GGA  ACA  GAT  TTC  ACA  TTA  ACC  ATC  AGC  AGT  CTG  CGG  CCT       240
Ser  Gly  Ser  Gly  Thr  Asp  Phe  Thr  Leu  Thr  Ile  Ser  Ser  Leu  Arg  Pro
 65                       70                       75                       80

GAA  GAC  ATT  GCC  ACT  TAC  TAC  TGT  CTA  CAG  GGT  CAA  AGT  TAT  CCT  CGT       288
Glu  Asp  Ile  Ala  Thr  Tyr  Tyr  Cys  Leu  Gln  Gly  Gln  Ser  Tyr  Pro  Arg
                      85                        90                       95

ACG  TTC  GGT  GGA  GGC  ACC  AAG  CTT  GAA  ATC  AAA                                 321
Thr  Phe  Gly  Gly  Gly  Thr  Lys  Leu  Glu  Ile  Lys
                100                      105
```

( 2 ) INFORMATION FOR SEQ ID NO: 8:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

Asp  Ile  Gln  Met  Asn  Gln  Ser  Pro  Ser  Ser  Leu  Ser  Ala  Ser  Leu  Gly
 1                   5                        10                       15

Asp  Thr  Ile  Thr  Ile  Thr  Cys  Arg  Ala  Arg  Leu  Asn  Ile  Asn  Ile  Trp
                 20                       25                      30

Leu  Ser  Trp  Tyr  Gln  Gln  Lys  Ala  Gly  Asn  Ile  Pro  Lys  Leu  Leu  Ile
            35                       40                       45

Ser  Lys  Ala  Ser  Asn  Leu  His  Thr  Gly  Val  Pro  Ser  Arg  Phe  Ser  Gly
       50                       55                       60

Ser  Gly  Ser  Gly  Thr  Asp  Phe  Thr  Leu  Thr  Ile  Ser  Ser  Leu  Arg  Pro
 65                       70                       75                       80

| Glu | Asp | Ile | Ala | Thr | Tyr | Tyr | Cys | Leu | Gln | Gly | Gln | Ser | Tyr | Pro | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Phe | Gly | Gly | Gly | Thr | Lys | Leu | Glu | Ile | Lys |
|-----|-----|-----|-----|-----|-----|-----|-----|-----|-----|-----|
|     |     |     | 100 |     |     |     |     | 105 |     |     |

( 2 ) INFORMATION FOR SEQ ID NO: 9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i i ) ANTI-SENSE: NO ( x i ) SEQUENCE DESCRIPTION: SEQ ID NO: 9:

AGGTGTCGAC TCCGAGGTGA AGCTGGTGGA GTCTGG    36

( 2 ) INFORMATION FOR SEQ ID NO: 10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i i ) ANTI-SENSE: YES ( x i ) SEQUENCE DESCRIPTION: SEQ ID NO: 10:

TCCAGGTCAA GGTCACTG    18

( 2 ) INFORMATION FOR SEQ ID NO: 11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) ANTI-SENSE: YES ( x i ) SEQUENCE DESCRIPTION: SEQ ID NO: 11:

GGAGACGGTG ACCGAGGTT    19

( 2 ) INFORMATION FOR SEQ ID NO: 12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i i ) ANTI-SENSE: NO ( x i ) SEQUENCE DESCRIPTION: SEQ ID NO: 12:

AGGTACGCGT TGTGACATCC AGATGAACCA GTCTCC    36

( 2 ) INFORMATION FOR SEQ ID NO: 13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i i ) ANTI-SENSE: YES ( x i ) SEQUENCE DESCRIPTION: SEQ ID NO: 13:

GCACACGACT GAGGCCACCT C    21

(2) INFORMATION FOR SEQ ID NO: 14:

(i) SEQUENCE CHARACTERISTICS:
(A) LENGTH: 21 base pairs
(B) TYPE: nucleic acid
(C) STRANDEDNESS: single
(D) TOPOLOGY: linear (iii) ANTI-SENSE: YES (xi) SEQUENCE DESCRIPTION: SEQ ID NO: 14:

CGTTTGATTT CAAGCTTGGT G                        21